(12) United States Patent
Waltman et al.

(10) Patent No.: US 6,963,773 B2
(45) Date of Patent: *Nov. 8, 2005

(54) H-BRIDGE CIRCUIT FOR GENERATING A HIGH-ENERGY BIPHASIC WAVEFORM IN AN EXTERNAL DEFIBRILLATOR USING SINGLE SCR AND IGBT SWITCHES IN AN INTEGRATED PACKAGE

(75) Inventors: Barry F. Waltman, Brier, WA (US); Joseph L. Sullivan, Kirkland, WA (US); Lawrence A. Borschowa, Woodinville, WA (US); Richard C. Nova, Kirkland, WA (US)

(73) Assignee: MedTronic Physio-Control Manufacturing Corp., Redmond, WA (US)

( * ) Notice: Subject to any disclaimer, the term of this patent is extended or adjusted under 35 U.S.C. 154(b) by 333 days.

This patent is subject to a terminal disclaimer.

(21) Appl. No.: 10/186,218

(22) Filed: Jun. 26, 2002

(65) Prior Publication Data

US 2004/0068301 A1 Apr. 8, 2004

Related U.S. Application Data

(63) Continuation-in-part of application No. 09/706,578, filed on Nov. 3, 2000, now Pat. No. 6,477,413, which is a continuation of application No. 09/287,483, filed on Apr. 6, 1999, now Pat. No. 6,175,765, which is a continuation-in-part of application No. 09/035,690, filed on Mar. 5, 1998, now Pat. No. 6,041,254, which is a continuation-in-part of application No. 08/811,833, filed on Mar. 5, 1997, now Pat. No. 5,824,017.

(51) Int. Cl.[7] .................................................. A61N 1/39
(52) U.S. Cl. ............................................ 607/5; 607/4
(58) Field of Search ..................................... 607/4–8

(56) References Cited

U.S. PATENT DOCUMENTS 1,662,771 A 3/1928 Whittingham
1,840,168 A 1/1932 Mucher (Continued)

FOREIGN PATENT DOCUMENTS

EP 0 315 768 5/1989
EP 0 553 864 A2 8/1993

(Continued)

OTHER PUBLICATIONS

G.H. Bardy et al., "Multicenter Comparison of Truncated Biphasic Shocks and Standard Damped Sine Wave Monophasic Shocks for Transthoracic Ventricular Defibrillation," *Circulation* 94(10):2507–2514, Nov. 15, 1996.

(Continued)

*Primary Examiner*—Jeffrey R. Jastrzab
(74) *Attorney, Agent, or Firm*—Mary Y. Redman

(57) ABSTRACT

An external defibrillator with an output circuit having four legs arrayed in the form of an "H" (an "H-bridge") is disclosed. The output circuit is designed to be able to conduct a range of defibrillation pulse energies, from below 50 joules to above 200 joules. Each leg of the output circuit contains a solid-state switch. By selectively switching on pairs of switches in the H-bridge, a biphasic defibrillation pulse may be applied to a patient. The switches in three of the legs of the H-bridge output circuit are preferably SCR switches, while the fourth leg includes an IGBT switch. In one embodiment, a single power switch is utilized in each of the legs of the H-bridge output circuit, and are included in a single integrated module or package. The use of single semiconductor switches in an integrated surface mountable module or package simplifies the assembly and manufacturing of the defibrillator device. The use of a single IGBT in a leg of the H-bridge (as opposed to two or more IGBTs in series) also greatly simplifies the drive circuitry required to turn on and off the IGBT.

23 Claims, 14 Drawing Sheets

U.S. PATENT DOCUMENTS

| | | | |
|---|---|---|---|
| 1,841,332 | A | 1/1932 | Kranz |
| 2,298,315 | A | 10/1942 | Siegel et al. |
| 2,464,820 | A | 3/1949 | Livera |
| 4,038,628 | A | 7/1977 | Salemi |
| 4,274,136 | A | 6/1981 | Onodera et al. |
| 4,402,322 | A | 9/1983 | Duggan |
| 4,693,253 | A | 9/1987 | Adams |
| 4,800,883 | A | 1/1989 | Winstrom |
| 4,821,723 | A | 4/1989 | Baker, Jr. et al. |
| 4,850,357 | A | 7/1989 | Bach, Jr. |
| 5,048,521 | A | 9/1991 | Pless et al. |
| 5,083,562 | A | 1/1992 | de Coriolis et al. |
| 5,099,844 | A | 3/1992 | Faupel |
| 5,358,512 | A | 10/1994 | Hoegnelid et al. |
| 5,376,103 | A | 12/1994 | Anderson et al. |
| 5,431,682 | A | 7/1995 | Hedberg |
| 5,431,684 | A | 7/1995 | Archer et al. |
| 5,431,686 | A | 7/1995 | Kroll et al. |
| 5,441,518 | A | 8/1995 | Adams et al. |
| 5,468,254 | A | 11/1995 | Hahn et al. |
| 5,470,341 | A | 11/1995 | Kuehn et al. |
| 5,489,293 | A | 2/1996 | Pless et al. |
| 5,507,781 | A | 4/1996 | Kroll et al. |
| 5,514,160 | A | 5/1996 | Kroll et al. |
| 5,522,853 | A | 6/1996 | Kroll |
| 5,531,765 | A | 7/1996 | Pless |
| 5,534,015 | A | 7/1996 | Kroll et al. |
| 5,591,209 | A | 1/1997 | Kroll |
| 5,591,210 | A | 1/1997 | Kroll et al. |
| 5,591,211 | A | 1/1997 | Meltzer |
| 5,591,213 | A | 1/1997 | Morgan |
| 5,593,427 | A | 1/1997 | Gliner et al. |
| 5,601,608 | A | 2/1997 | Mouchawar |
| 5,601,612 | A | 2/1997 | Gliner et al. |
| 5,607,454 | A | 3/1997 | Cameron et al. |
| 5,620,465 | A | 4/1997 | Olson et al. |
| 5,674,266 | A | 10/1997 | Stendahl |
| 5,733,310 | A | 3/1998 | Lopin et al. |
| 5,824,017 | A * | 10/1998 | Sullivan et al. ............... 607/5 |
| 5,873,893 | A | 2/1999 | Sullivan et al. |
| 5,879,374 | A | 3/1999 | Powers et al. |
| 6,041,254 | A * | 3/2000 | Sullivan et al. ............... 607/5 |
| 6,175,765 | B1 * | 1/2001 | Sullivan et al. ............... 607/5 |
| 6,208,895 | B1 | 3/2001 | Sullivan et al. |
| 6,477,413 | B1 * | 11/2002 | Sullivan et al. ............... 607/5 |

FOREIGN PATENT DOCUMENTS

| | | |
|---|---|---|
| EP | 0 747 093 A2 | 12/1996 |
| WO | WO 93/16759 | 9/1993 |
| WO | WO 94/27674 | 12/1994 |
| WO | WO 95/05215 | 2/1995 |
| WO | WO 95/09673 | 4/1995 |
| WO | WO 98/39060 A1 | 9/1998 |
| WO | WO 98/39061 A3 | 9/1998 |

OTHER PUBLICATIONS

G.H. Bardy et al., "Truncated Biphasic Pulses for Transthoracic Defibrillation," *Circulation* 91(6):1768–1774, Mar. 15, 1995.

R.O. Cummins et al., Overview, "Ventricular Fibrillation, Automatic External Defibrillators, and the United States Food and Drug Administration: Confrontation Without Comprehension," *Annals of Emergency Medicine* 26(5):621, 631, Nov. 1995.

S.A. Feeser et al., Abstract, "Strength–Duration and Probability of Success Curves for Defibrillation With Biphasic Waveforms," *Circulation* 82:2128–2141, 1990.

B.E. Gliner et al., "Transthoracic Defibrillation of Swine with Monophasic and Biphasic Waveforms," *Circulation* 92(6):1634–1643, Sep. 15, 1995.

Kroll, M.W., "A Minimal Model of the Single Capacitor Biphasic Defibrillation Waveform," *PACE* 17(1):1782–1792, Nov. 1994.

A.S.L. Tang et al., Abstract, "Ventricular Defibrillation Using Biphasic Waveforms: The Importance of Phasic Duration," *Journal of American College of Cardiology* 13(1):207–214, Jan. 1989.

G.P. Walcott et al., "Choosing the Optimal Monophasic and Biphasic Waveforms for Ventricular Defibrillation," *Journal of Cardiovascular Electrophysiology* 6(9):737–750, Sep. 1995.

"Defibrillator," a Russian defibrillator manual (in English), 1994, 10 pages.

"Portable Defibrillator with General–Purpose Power Supply," an advertising brochure for a Russian defibrillator of in Russian and English), 1994, 4 pages.

* cited by examiner

H-BRIDGE CIRCUIT FOR GENERATING A HIGH-ENERGY BIPHASIC WAVEFORM IN AN EXTERNAL DEFIBRILLATOR USING SINGLE SCR AND IGBT SWITCHES IN AN INTEGRATED PACKAGE

CROSS-REFERENCES TO RELATED APPLICATIONS

This application is a continuation-in-part of prior application Ser. No. 09/706,578, filed Nov. 3, 2000 now U.S. Pat. No. 6,477,413, which is a continuation of prior application Ser. No. 09/287,483, filed Apr. 6, 1999, now U.S. Pat. No. 6,175,765, which is a continuation-in-part of prior application Ser. No. 09/035,690, filed Mar. 5, 1998, now U.S. Pat. No. 6,041,254, which is a continuation-in-part of prior application Ser. No. 08/811,833, filed Mar. 5, 1997, now U.S. Pat. No. 5,824,017, priority from the filing dates of which is hereby claimed under 35 U.S.C. § 120.

FIELD OF THE INVENTION

This invention relates generally to apparatus for generating defibrillation waveforms, and more particularly to a circuit for generating a biphasic defibrillation waveform in an external defibrillator.

BACKGROUND OF THE INVENTION

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a high-energy transfer relay. A discharge control signal causes the relay to complete an electrical circuit between the storage capacitor and a wave shaping circuit whose output is connected to the electrodes attached to the patient.

The relay used in contemporary external defibrillators has traditionally allowed a monophasic waveform to be applied to the patient. It has recently been discovered, however, that there may be certain advantages to applying a biphasic rather than a monophasic waveform to the patient. For example, preliminary research indicates that a biphasic waveform may limit the resulting heart trauma associated with the defibrillation pulse.

The American Heart Association has recommended a range of energy levels for the first three defibrillation pulses applied by an external defibrillator. The recommended energy levels are: 200 joules for a first defibrillation pulse; 200 or 300 joules for a second defibrillation pulse; and 360 joules for a third defibrillation pulse, all within a recommended variance range of no more than plus or minus 15 percent according to standards promulgated by the Association for the Advancement of Medical Instrumentation (AAMI). These high energy defibrillation pulses are required to ensure that a sufficient amount of the defibrillation pulse energy reaches the heart of the patient and is not dissipated in the chest wall of the patient.

Some implantable defibrillators, such as those shown in U.S. Pat. Nos. 5,083,562 and 4,880,357, use a bridge circuit with multiple silicon-controlled rectifiers (SCRs) to generate a biphasic waveform. Because implantable defibrillators only apply a low energy defibrillation pulse having a maximum energy of approximately 35 joules, however, the output circuit in implantable defibrillators is not adaptable for use in the external defibrillator. A 200 joule energy pulse applied to an implantable defibrillator bridge circuit would overload the bridge circuit components and cause the circuit to fail.

On the other hand, pacers are typically used to administer a series of relatively small electrical pulses to a patient experiencing an irregular heart rhythm. For example, each pacing pulse typically has an energy of about 0.05J to 1.2J. Because of the small energies used for pacing pulses, the circuitry used to generate the pacing pulses cannot typically be used for generating defibrillation pulses, which are typically of much higher energies and currents.

There are some systems that combine both a pacer and a defibrillator in a single unit for providing pacing pulses and defibrillation pulses as required. These conventional systems typically use separate defibrillation and pacing generation circuits. Implantable systems generally use separate electrodes for pacing and defibrillation. An example of an implantable combined defibrillator/pacer is found in U.S. Pat. No. 5,048,521. Of course, having separate defibrillation and pacing circuits tends to increase the cost and size of the unit. In addition, because implantable defibrillators and pacers typically apply relatively low energy pulses, the output circuitry for such implantable units is generally not adaptable for use in an external unit.

In addition, conventional external defibrillator circuits have typically been large and expensive, due in part to the components required to conduct the large energy pulses that are generated in external defibrillators. It would be desirable to reduce the size and expense of such external defibrillator circuits.

The present invention is directed to providing apparatus that overcome the foregoing and other disadvantages. More specifically, the present invention is directed to an output circuit for an external defibrillator that is capable of applying a high-energy biphasic defibrillation pulse to a patient, and which has a reduced overall parts count, thus improving reliability and manufacturability of the external defibrillator.

SUMMARY OF THE INVENTION

An external defibrillator having an output circuit that allows a biphasic defibrillation pulse to be discharged to a patient from an energy storage device, preferably an energy storage capacitor, is disclosed. The output circuit includes four legs arrayed in the form of an "H" (hereinafter the "H-bridge output circuit"). Each leg of the output circuit contains a solid-state switch. By selectively switching on pairs of switches in the H-bridge output circuit, a biphasic defibrillation pulse may be applied to the patient.

In accordance with one aspect of the invention, the switches in three of the legs of the H-bridge output circuit are silicon controlled rectifiers (SCRs). Preferably, only a single SCR is used in each leg. The switch in the fourth leg is an insulated gate bipolar transistor (IGBT). In one embodiment, two IGBTs may be coupled in series in the fourth leg, while in another embodiment only a single IGBT is used in the fourth leg. The use of single SCR and IGBT switches in each leg simplifies the circuit as compared to the use of semiconductor modules that are large and expensive or as compared to the use of lower voltage parts which must be stacked. The use of three SCR legs further reduces the size, weight, and cost of the H-bridge output circuit in comparison with an implementation using two SCR and two IGBT legs. The use of a single IGBT in a leg of the H-bridge (as opposed to two or more IGBTs in series) also greatly simplifies the drive circuitry required to turn on and off the IGBT.

In accordance with still another aspect of the invention, a single power switch is utilized in each of the legs of the H-bridge output circuit, and are included in a single integrated module or package. The use of single semiconductor switches in an integrated surface mountable module or package simplifies the assembly and manufacturing of the defibrillator device.

In accordance with another aspect of the invention, the H-bridge output circuit is capable of conducting a biphasic waveform of 200 or more joules from the energy storage capacitor to the patient. Preferably, the H-bridge output circuit is capable of conducting a biphasic waveform equal to 360 joules, the industry standard for monophasic waveforms and the recommended level for a third defibrillation pulse by the American Heart Association. To store sufficient energy for such a biphasic defibrillation pulse, the size of the energy storage capacitor may in one embodiment fall within a range from 150 uF to 200 uF.

Moreover, in addition to being able to conduct a high energy defibrillation pulse of 200 to 360 joules, the H-bridge output circuit is also capable of conducting a low energy defibrillation pulse for internal applications with an energy as low as 1 to 50 joules. Low energy defibrillation pulses are required when, for example, internal paddles are coupled to the defibrillator for use in surgery to directly defibrillate the heart, or for pediatric defibrillation, or for cardioversion of some arrhythmias in both pediatrics and adults. To allow the delivery of a low energy defibrillation pulse, in one embodiment the output circuit switches in one or more of the legs are driven by gate drive circuits which provide a repetitively pulsed control signal to the gates of the switches. The pulsed control signal on the gates allows the high voltage switches to remain conducting even when conducting very low currents.

In accordance with another aspect of the invention, a gate drive circuit biases on the IGBT in the fourth leg with a sufficient voltage over a short interval to allow the leg to conduct a high current without being damaged. In one embodiment, the leg can conduct a current of at least approximately 200 amps, while in another embodiment a current of at least approximately 400 amps can be conducted. Biasing the IGBTs in this manner allows the IGBTs to withstand a high energy discharge such as occurs when a low resistance load is placed at the output of the circuit.

In accordance with still another aspect of the invention, all of the output circuit switches are selected to have sufficient current conducting capability to allow the switches in two of the legs on the same side of the H-bridge to provide a shorted path for the discharge of unwanted energy from the energy storage capacitor. The use of two legs on one side of the H-bridge to discharge the capacitor eliminates the need for an additional discharge circuit to perform this internal energy dump function. In addition, the H-bridge circuit is able to perform the internal energy dump quickly and accurately using advantageous component values that would not be practical to implement in a separate discharge circuit. For example, the H-bridge circuit is able to perform an internal dump in less than one second through the use of a resistive component with a value of less than 100 ohms. Also, the internal dump may be performed using the H-bridge circuit so as to discharge only a specified amount of energy from the storage capacitor, rather than discharging the storage capacitor completely. Also, because the H-bridge circuit is used for both the internal dump and defibrillation pulse operations, the resistive component of the H-bridge circuit serves to both absorb energy during the internal dump and also to limit current during the defibrillation pulse. The resistive value is selected to be small enough to allow sufficient current to provide both an effective defibrillation pulse and a fast internal energy dump, while also being large enough to limit the current so as to protect the switches of the H-bridge circuit. The resistive component is also selected to have a high thermal capacity so that it can withstand the heat produced by the high currents that result during the H-bridge internal dump and defibrillation pulse circuit operations.

In accordance with another aspect of the invention, the resistive component of the H-bridge circuit is incorporated into a protective component that limits both current and voltage changes from the energy storage capacitor. The protective component is designed with both inductive and resistive properties. The use of a single protective component with these properties reduces the number of components that are required in the H-bridge circuit. In accordance with yet another aspect of the invention, in one embodiment the gate drive circuit provides a slow turn-on and fast turn-off of the IGBTs. The slow turn-on avoids jolting an electrically coupled SCR on one of the other H-bridge output circuit legs into a conducting state. The fast turn-off reduces the exposure of the IGBTs to potentially damaging high voltages that can occur across one IGBT when the other IGBT is inadvertently turned off first. The IGBT gate drive circuitry therefore reduces the size of the high-voltage parts that are necessary to protect the IGBTs.

In accordance with another aspect of the invention, prior to application of the defibrillation pulse, the integrity of each of the switches in the output circuit is verified in that each of the legs in the output circuit is checked by switching the switches on in a desired order while the energy storage capacitor is partially charged. The integrity of the output circuit during the application of a defibrillation pulse is also verified by monitoring the changing charge level of the energy storage capacitor.

In accordance with another aspect of the invention, the integrity of the H-bridge is monitored during application of the defibrillation pulse by periodically measuring the voltage across the energy storage capacitor. A voltage outside an expected range may indicate the failure of the H-bridge.

In accordance with still another aspect of the invention, a failed leg in the H-bridge is compensated for by identifying a pair of legs that provides a conductive path between the energy storage capacitor and the patient. If an operational pair of legs is identified, the defibrillator delivers a monophasic, rather than a biphasic, defibrillation pulse. The current or duration of the monophasic pulse may also be altered by changing the charge on the energy storage capacitor.

In accordance with yet another aspect of the invention, a scaling circuit is provided to step down the voltage across the energy storage capacitor so that it can be measured by the microprocessor. The scaling circuit is adjustable to allow the microprocessor to measure various voltage ranges across the energy storage capacitor.

In accordance with another aspect of the invention, if any error is detected before or during delivery of the defibrillation pulse, an error handling routine may be called to analyze and attempt to compensate for the indicated failure. The error handing routine generates a visual, aural, or other warning to the user to indicate that the defibrillator is not functioning properly. The warning to the user is especially advantageous under circumstances where the user might not otherwise be aware that the defibrillator is not functioning properly.

In accordance with still another aspect of the invention, the pacing current is conducted through one of the SCRs of the H-bridge. A drive circuit for the SCR is derived such that the SCR may be continuously driven on for either a biphasic waveform pulse or a pace waveform pulse. The drive circuit is able to hold on the high power SCR at current levels well below the holding current levels of the SCR, such as may occur during pacing applications. Additionally, for delivering the high energy biphasic defibrillation waveform, the drive circuit has sufficient drive level to turn on the high power SCR for delivering the high energy defibrillation waveform. This topology is advantageous in that a single power switch can be utilized for generating the pace waveform pulse or the biphasic waveform pulse, thus reducing the total number of parts required to implement both biphasic and pacing waveform generation.

In accordance with yet another aspect of the invention, the H-bridge output circuit conducts the pacing waveform through a combination of one upper leg SCR of the H-bridge and a current source. The current source is configured to essentially bypass one of the lower leg SCRs of the H-bridge.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
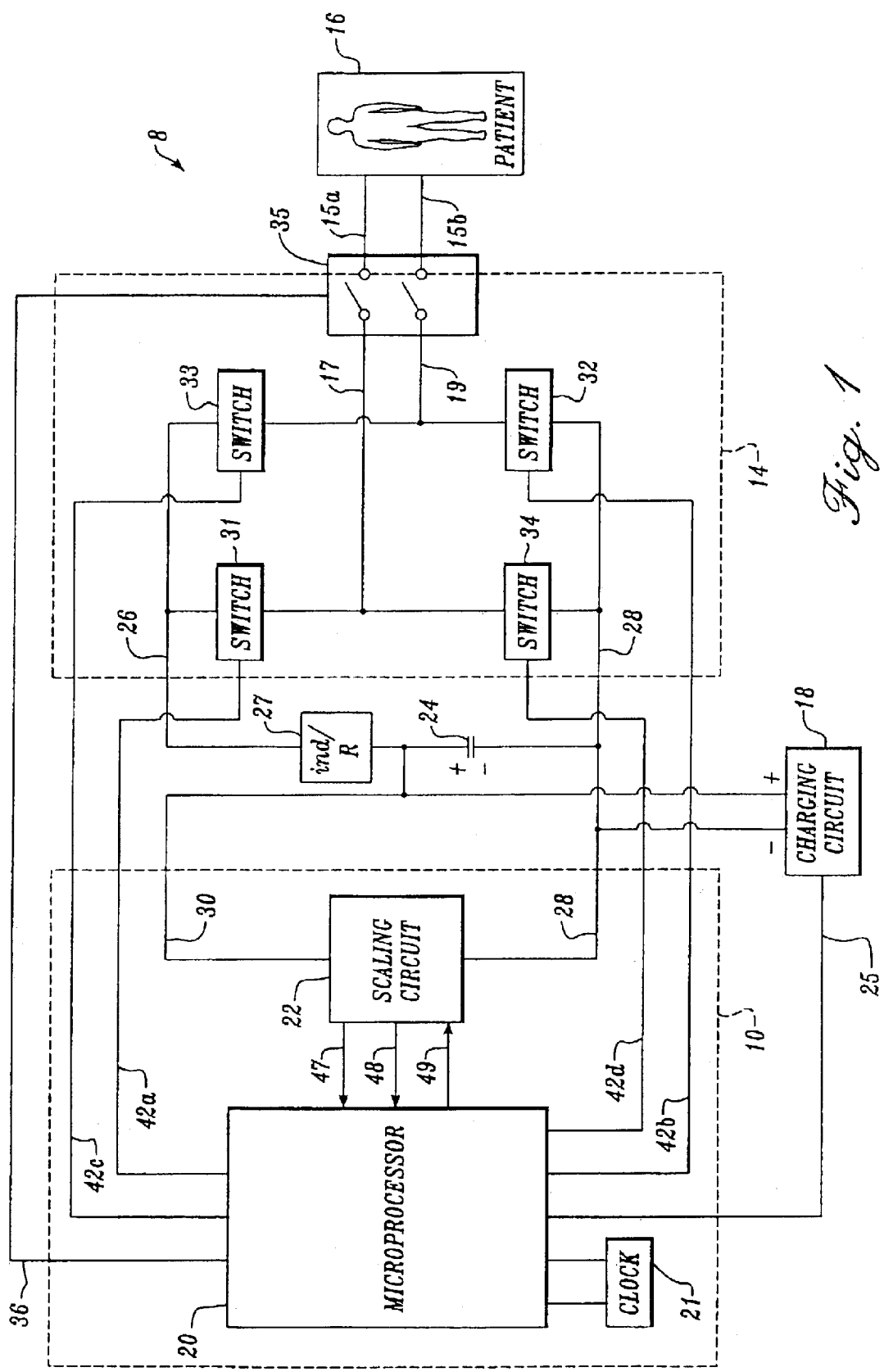
FIG. 1 is a block diagram of an external defibrillator having an output circuit suitable for delivering a high-energy biphasic defibrillation pulse to a patient.

FIG. 1 is a block diagram of an external defibrillator 8 that is connected to a patient 16. The defibrillator includes a microprocessor 20 that is connected to an energy storage capacitor 24 via a charging circuit 18. During the operation of the defibrillator, the microprocessor controls the charging circuit 18 by a signal on a control line 25 to charge the energy storage capacitor to a desired voltage level. To monitor the charging process, the microprocessor is connected to a scaling circuit 22 by a pair of measurement lines 47 and 48, and by a control line 49. The scaling circuit 22 is connected to the energy storage capacitor 24 by a bridge line 28, which connects to the negative lead of the capacitor, and by a line 30, which connects to the positive lead of the capacitor. A clock 21 is also connected to the microprocessor 20.

The scaling circuit 22 is used to step down the voltage across the energy storage capacitor 24 to a range that may be monitored by the microprocessor. The scaling circuit 22 is described briefly below and in more detail both in FIG. 6 of this application and in an application entitled "Method and Apparatus for Verifying the Integrity of an Output Circuit Before and During Application of a Defibrillation Pulse," Ser. No. 08/811,834, filed Mar. 5, 1997, now U.S. Pat. No. 5,873,893, and hereby incorporated by reference. The energy storage capacitor 24 can be charged to a range of voltage levels, with the selected level depending on the patient and other parameters. Preferably, the size of the energy storage capacitor falls within a range from 150 uF to 200 uF. In order to generate the necessary defibrillation pulse for external application to a patient, the energy storage capacitor is charged to between 100 volts and 2,200 volts. To detect small percentage changes in the selected voltage level of the energy storage capacitor 24, the scaling circuit is adjustable to measure different voltage ranges. The adjusted output is measured by the microprocessor 20 on measurement line 48.

After charging to a desired level, the energy stored in the energy storage capacitor 24 may be delivered to the patient 16 in the form of a defibrillation pulse. An output circuit 14 is provided to allow the controlled transfer of energy from the energy storage capacitor to the patient. The output circuit 14 includes four switches 31, 32, 33, and 34, each switch on a leg of the output circuit arrayed in the form of an "H" (hereinafter the "H-bridge" output circuit). Switches 31 and 33 are coupled through a protective component 27 to the positive lead of the energy storage capacitor 24 by a bridge line 26. The protective component 27 limits the current and voltage changes from the energy storage capacitor 24, and has both inductive and resistive properties. Switches 32 and 34 are coupled to the energy storage capacitor 24 by a bridge line 28. The patient 16 is connected to the left side of the H-bridge by an apex line 17, and to the right side of the H-bridge by a sternum line 19. As depicted in FIG. 1, the apex line 17 and the sternum line 19 are connected to electrodes 15a and 15b, respectively, by a patient isolation relay 35. The microprocessor 20 is connected to the switches 31, 32, 33, and 34 by control lines 42a, 42b, 42c, and 42d, respectively, and to the patient isolation relay 35 by control line 36. Application of appropriate control signals by the microprocessor over the control lines causes the switches to be opened and closed, and the output circuit 14 to conduct energy from the energy storage capacitor 24 to the patient.

Figure 2:
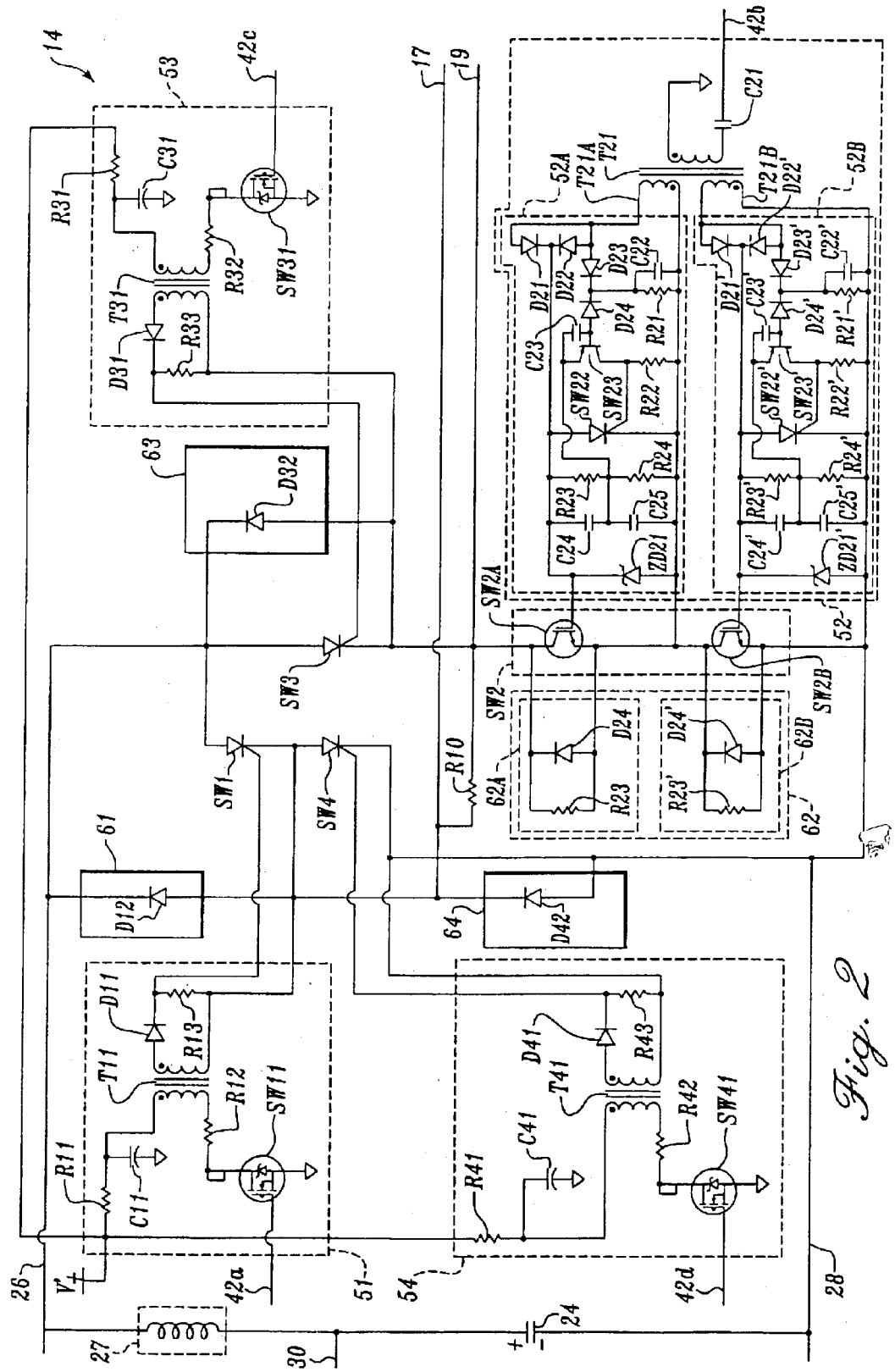
FIG. 2 is a schematic diagram of the preferred embodiment of the output circuit of FIG. 1.

A preferred construction of the output circuit 14 is shown in FIG. 2. The output circuit relies on four output switches SW1 to SW4 to conduct energy from the energy storage capacitor 24 to the patient. Switches SW1, SW3 and SW4 are semiconductor switches, preferably silicon controlled rectifiers (SCRs). Switch SW2 is a series combination of switches SW2A and SW2B, preferably both insulated gate bipolar transistors (IGBTs). Two IGBTs are required because the limitations of IGBT switch technology are such that the maximum working voltage of presently available IGBTs is not sufficient to withstand the maximum voltage that may occur across switch SW2 in output circuit 14. Switch SW2 is therefore constructed with two IGBT switches that are connected in series so that the voltage across the entire switch SW2 is divided between the two IGBT switches. Those skilled in the art will appreciate that a single IGBT may be used in the output circuit, should an IGBT having a sufficient voltage rating become available. The four output switches SW1 to SW4 can be switched from an off (non-conducting) to an on (conducting) condition.

Defibrillator 8 generates a biphasic defibrillation pulse for application to the patient 16. When the energy storage capacitor 24 is charged to a selected energy level and the patient isolation relay 35 is closed, the switches SW1 and SW2 are switched on so as to connect the energy storage capacitor with the apex line 17 and sternum line 19 for the application of a first phase of a defibrillation pulse to the patient. The stored energy travels from the positive terminal of the energy storage capacitor 24 on line 26, through switch SW1 and apex line 17, across the patient 16, and back through sternum line 19 and switch SW2 to the negative terminal of the capacitor on line 28. The first phase of the biphasic pulse is therefore a positive pulse from the apex to the sternum of the patient.

Before the energy storage capacitor 24 is completely discharged, the switch SW2 is biased off to prepare for the application of the second phase of the biphasic pulse. Once the switch SW2 is biased off, switch SW1 will also become non-conducting because the voltage across the SCR falls to zero.

After the end of the first phase of the biphasic defibrillation pulse, switches SW3 and SW4 are switched on to start the second phase of the biphasic pulse. Switches SW3 and SW4 provide a path to apply a negative defibrillation pulse to the patient 16. The energy travels from the positive terminal of the energy storage capacitor 24 on line 26, through switch SW3 and sternum line 19, across the patient 16, and back through apex line 17 and switch SW4 to the negative terminal of the energy storage capacitor on line 28. The polarity of the second phase of the defibrillation pulse is therefore opposite in polarity to the first phase of the biphasic pulse. The end of the second phase of the biphasic pulse is truncated by switching on switch SW1 to provide a shorted path for the remainder of the capacitor energy through switches SW1 and SW4. After the second phase is truncated, all four of the switches SW1 to SW4 are switched off and the patient isolation relay 35 is opened. The energy storage capacitor 24 may then be recharged to prepare the defibrillator to apply another defibrillation pulse.

As described above, the four output switches SW1 to SW4 can be switched from an off (nonconducting) state to an on (conducting) state by application of appropriate control signals on control lines 42a, 42b, 42c, and 42d. In order to allow the SCRs and IGBTs to switch the high voltages in an external defibrillator, special switch driving circuits 51, 52, 53 and 54 are coupled to switches SW1 to SW4, respectively. The control lines 42a, 42b, 42c, and 42d are connected to the switch driving circuits 51, 52, 53, and 54, to allow the microprocessor to control the state of the switches.

Switch driving circuits 51, 53 and 54 are identical. For purposes of this description, therefore, only the construction and operation of switch driving circuit 51 will be described. Those skilled in the art will recognize that switch driving circuits 53 and 54 operate in a similar manner.

Switch driving circuit 51 includes control switch SW11, resistors R11, R12, and R13, capacitor C11, diode D11 and high-voltage transformer T11. Resistor R11 is connected between the positive voltage supply V'+ and the dotted end of the primary winding of transformer T11, and capacitor C11 is connected between ground and the dotted end of the primary winding of transformer T11. Resistor R12 is connected between the non-dotted end of the primary winding of transformer T11 and the drain of the control switch SW11. Resistors R11 and R12 and capacitor C11 limit and shape the current and voltage waveforms across the primary winding of the transformer T11. The source of the control switch SW11 is connected to ground, and the gate of control switch SW11 is connected to control line 42a.

On the secondary winding side of transformer T11, the anode of diode D11 is connected to the dotted end of the secondary winding of transformer T11, and the cathode of diode D11 is connected to the gate of the SCR switch SW1. Resistor R13 is connected between the cathode of diode D11 and the non-dotted end of the secondary winding of the transformer T11. The non-dotted end of the secondary winding of transformer T11 is connected to the cathode of the SCR switch SW1.

To turn on switch SW1, an oscillating control signal, preferably a pulse train, is provided on control line 42a. The pulse train control signal repeatedly turns control switch SW11 on and off, producing a changing voltage across the primary winding of the transformer T11. The voltage is stepped down by the transformer T11 and rectified by the diode D11 before being applied to the SCR switch SW1. In the preferred embodiment, a 10% duty cycle pulse train on the control line 42a has been found to be adequate to maintain the SCR switch SW1 in a conducting state. As long as the control signal is applied to the switch driving circuit 51, the switch SW1 will remain in the conducting state. The switch SW1 remains in the conducting state even when conducting only very low currents, such as the current associated with a low-energy defibrillation pulse.

A different switch driving circuit is required to turn on the IGBT switches of switch SW2. Switch driving circuit 52 includes a capacitor C21, a transformer T21, and two identical switch driving circuits 52A and 52B, each circuit corresponding to one of the IGBTs. On the primary winding side of the transformer T21, capacitor C21 is connected between the control line 42b and the non-dotted end of the primary winding of the transformer T21. The dotted end of the primary winding of the transformer T21 is connected to ground.

Transformer T21 has two secondary windings T21A and T21B, one for each of the switch driving circuits 52A and 52B. Switch driving circuits 52A and 52B are identical, and therefore only the construction and operation of switch driving circuit 52A will be described. Switch driving circuit 52A includes diodes D21, D22, D23, and D24, Zener diode ZD21, capacitors C22, C23, C24, and C25, resistors R21, R22, R23, and R24, a PNP switch SW23, and an SCR switch SW22.

The anodes of the diodes D21, D22, and D23 are connected to the non-dotted end of the secondary winding T21A of the transformer T21. The cathodes of diodes D21 and D22 are connected to the gate of the IGBT switch SW2A. The resistor R21 and capacitor C22 are connected between the dotted end of the secondary winding T21A of the transformer T21 and the cathode of diode D23. The anode of the SCR switch SW22 and the cathode of Zener diode ZD21 are connected to the gate of the IGBT switch SW2A. The cathode of the SCR switch SW22 and the anode of the Zener diode ZD21 are connected to the dotted end of the secondary winding T21A of the transformer T21, and also to the emitter of the IGBT switch SW2A.

The resistor R23 and the capacitor C24 are connected between the gate of the IGBT switch SW2A and the emitter of the PNP switch SW23. The resistor R24 and the capacitor C25 are connected between the emitter of the PNP switch SW23 and the dotted end of the secondary winding T21A of the transformer T21. The gate of the SCR switch SW22 is connected to the collector of the PNP switch SW23. The resistor R22 is connected between the collector of the PNP switch SW23 and the dotted end of the secondary winding T21A of the transformer T21. The capacitor C23 is connected between the emitter and the base of the PNP switch SW23. The anode of the diode D24 is connected to the base of the PNP switch SW23, and the cathode of the diode D24 is connected to the cathode of the diode D23.

To turn on the IGBT switch SW2A, an oscillating control signal, preferably a pulse train, is provided on control line 42b. The pulse train control signal is stepped up in voltage by the transformer T21 and applied to the input of switch driving circuit 52A. During a positive pulse of the control signal on control line 42b, diodes D21 and D22 rectify the current that travels through the secondary winding T21A to charge capacitors C24 and C25. As will be discussed in more detail below, some current also travels through diode D23 to charge capacitor C22.

Capacitor C21 limits the current in the primary winding of the transformer T21, which correspondingly limits the current in the secondary winding T21A. The secondary winding current determines the charging time of the capacitors C24 and C25. Since the voltage across the capacitors C24 and C25 is also the voltage on the gate of the IGBT switch SW2A, a slow accumulation of voltage on the capacitors C24 and C25 therefore results in a slow turn on of the IGBT switch SW2A. The charging current is selected so that the IGBT switch SW2A is turned on relatively slowly when compared to the fast turn on of the SCR switches SW1, SW3, and SW4. A slow turn-on for the IGBT switch SW2A is desirable because the IGBT switches are on the same side of the H-bridge output circuit 14 as SCR switch SW3. SCR switch SW3 is controlled by the control signal on control line 42c, but due to the nature of SCR switches, the SCR switch may be accidentally turned on regardless of the signal on control line 42c if a rapid voltage change occurs across SCR switch SW3. If IGBT switches SW2A and SW2B were therefore turned on too quickly, the resulting rate of change of the voltage across SCR switch SW3 might cause it to turn on accidentally.

Zener diode ZD21 protects the IGBT switch SW2A by regulating the maximum voltage across the capacitors C24 and C25. Without Zener diode ZD21, the voltage on the gate of IGBT switch SW2A would rise to a level that would damage IGBT switch SW2A.

Also during the positive pulse of the pulse train control signal on control line 42b, diode D23 rectifies the current that travels through the secondary winding T21A to charge capacitor C22. The charge on capacitor C22, which is replenished on each positive pulse of the pulse train control signal, maintains the voltage across the base of the PNP switch SW23 above the turn-on level for the PNP switch. The PNP switch SW23 turns on if the base voltage on the switch drops below a threshold level. As will be described below, the PNP switch SW23 is only turned on when the IGBT switch SW2A is to be turned off. Capacitor C23 and diode D24 are also provided to prevent PNP switch SW23 from turning on. Capacitor C23 serves as a high frequency filter to prevent the high frequency driving pulses of the switch driving circuit 52A from causing the PNP switch to spuriously turn on. Diode D24 prevents a large negative base-emitter voltage from occurring which could cause the PNP switch to enter reverse breakdown.

Since some discharging of the capacitor C22 occurs through resistor R21 between positive pulses of the control signal on control line 42b, resistor R21 must be large enough to limit the discharging current flow from the capacitor C22 between the pulses. Limiting the current flow prevents the voltage on capacitor C22 from dropping below the threshold level sufficient to turn on PNP switch SW23 between pulses of the control signal. Then, during a positive pulse of the pulse train control signal on control line 42b, the charging of capacitor C22 must be sufficient to counteract the discharging that occurred since the previous positive pulse so as to return the capacitor C22 to its fully charged level by the end of the positive pulse.

In the preferred embodiment, a 2 MHz pulse train control signal with a 25% duty cycle on the control line 42b has been found to be adequate to maintain the conducting state of the IGBT switches SW2A and SW2B. The switches will remain conducting as long as the control signal is present, and regardless of the current flowing through the switches.

The maximum current that may generally occur in the output circuit 14 results from the undesirable situation where a user of the defibrillator places the two shock paddles directly in contact with one another. When this happens, a short circuit is created between the apex line 17 and the sternum line 19. During a short circuit, a brief current of up to 400 amps can result. To accommodate the -short circuit current without damaging IGBT switches SW2A and SW2B, the IGBT switches SW2A and SW2B are biased by a 30V gate voltage. Biasing the IGBTs at this voltage level is successful since the IGBT switches are used in a pulsed manner. If the IGBT switches were driven continuously for long periods of time with 30V on their gates, they might be damaged, but in the defibrillator output circuit they are only driven at this level for very brief intervals.

In contrast to the slow turn-on of the IGBT switches SW2A and SW2B, the turn-off of the IGBT switches is performed relatively quickly. The IGBT switches may be quickly turned off because at turn-off there is no concern that the sensitive SCR switches will accidentally turn on. In addition, a fast turn-off is desirable to reduce the time that an IGBT switch would be subjected to a high voltage if one of the IGBT switches is inadvertently turned off before the other.

The IGBT switches are turned off when the pulse train control signal on the control line 42b is removed. Once positive voltage pulses are no longer being induced in the secondary windings of the transformer T21, the driving circuits 52A and 52B begin the turn-off process. Again, the turn-off process will only be described with respect to driving circuit 52A since the circuits are identical.

During the turn-off process, capacitor C22 begins discharging through resistor R21. Since the RC time constant of capacitor C22 and resistor R21 is much smaller than the RC time constant of capacitors C24 and C25 and resistors R23 and R24, the discharging of the capacitor C22 occurs much more quickly than the discharging of the capacitors C24 and C25. When the voltage on the capacitor C22 drops below a threshold voltage level, PNP switch SW23 is turned on. The threshold voltage level is equivalent to the base turn-on voltage of the PNP switch SW23, plus the voltage drop across diode D24. Once PNP switch SW23 is turned on, discharge current from the capacitor C25 begins to flow through the switch. As the current increases, the voltage across resistor R22 correspondingly increases. When the voltage across resistor R22 reaches a sufficient voltage level, SCR switch SW22 is turned on, providing a shorted path for the remainder of the energy stored in capacitors C24 and C25. The rapid discharge of the capacitors C24 and C25 causes a corresponding rapid drop in the gate voltage of the IGBT switch SW2A, quickly turning off the switch. Resistors R23 and R24 are provided across capacitors C24 and C25 to control the voltage division across the capacitors.

It will be appreciated that the special driving circuits 52A and 52B allow the IGBTs to be used in an external defibrillator where extremely high voltages must be switched in the presence of SCRs. The driving circuits minimize the number of components required to switch a defibrillation pulse of 200 or more joules. In addition to conducting high currents associated with high-energy defibrillation pulses, the IGBTs are also able to conduct very low currents that are associated with defibrillation pulses of less than 50 joules.

As shown in FIG. 2, each switch SW1 to SW4 is also connected in parallel with a switch protection circuit 61, 62, 63, and 64, respectively. The switch protection circuits are designed to prevent spurious voltage spikes from damaging the switches in the output circuit 14. Switch protection circuits 61, 63 and 64 are identical and therefore only the construction and operation of switch protection circuit 61 will be described. Switch protection circuit 61 includes a diode D12. The cathode of the diode D12 is connected to the anode of SCR switch SW1, and the anode of the diode D12 is connected to the cathode of SCR switch SW1. Diode D12 protects SCR switch SW1 against negative inductive spikes that may occur due to cable or load inductance.

Switch protection circuit 62 includes two identical switch protection circuits 62A and 62B, which protect IGBT switches SW2A and SW2B, respectively. Since switch protection circuits 62A and 62B are identical, only the construction and operation of switch protection circuit 62A will be described. Switch protection circuit 62A includes a diode D24 and a resistor R23. The resistor R23 is connected between the collector and the emitter of IGBT switch SW2A. The cathode of diode D24 is connected to the collector of IGBT switch SW2A, and the anode of diode D24 is connected to the emitter of IGBT switch SW2A.

Diode D24 operates similarly to diode D12 as described above in that it protects IGBT switch SW2A against negative inductive spikes. Resistor R23 (in conjunction with resistor R23') ensures that the voltage across the two IGBT switches SW2A and SW2B is equally divided when the output circuit 14 is at rest. Dividing the voltage across the two IGBT switches SW2A and SW2B is important due to the limitations of present IGBT technology, which limits the rating of each IGBT switch to 1200V. In a system where the total maximum voltage is 2200V, the maximum voltage ratings are therefore obeyed by dividing the maximum voltage across each IGBT switch.

Additional protection to the switches is provided by the protective component 27, which has both inductive and resistive properties. The protective component 27 limits the rate of change of the voltage across, and current flow to, the SCR switches SW1, SW3, and SW4. Too high of a rate of change of the voltage across an SCR switch is undesirable because it can cause the SCR switch to inadvertently turn on. For example, since SCR switches SW1 and SW4 are on the same side of the H-bridge output circuit 14, any time SCR switch SW4 is abruptly turned on, a rapid voltage change may also result across SCR switch SW1. To prevent rapid voltage changes, protective component 27 reduces the rate of change of the voltage across SCR switch SW1 when SCR switch SW4 is turned on. Also, too high of a current flow can damage the switches SW1, SW3 and SW4, and protective component 27 limits the current flow in the output circuit 14. The use of protective component 27 therefore reduces the need for additional protective components that would otherwise need to be coupled to the switches SW1, SW3 and SW4.

In some circumstances, it may be desirable for the defibrillator 8 to have a means for internally discharging energy from the energy storage capacitor 24. As an example, if the energy storage capacitor 24 was initially charged to the 360 joule level in preparation for applying an external defibrillation pulse, but then defibrillator was taken into surgery and was needed for applying a 2 joule internal pulse, a significant amount of energy would need to be dumped from the capacitor 24. Prior art circuits have typically required a separate internal dump circuit to perform this function. However, as described above for the present invention, unwanted energy on the storage capacitor 24 may be discharged by causing the switches on two of the legs on the same side of the H-bridge circuit (i.e., switches SW1 and SW4 or else switches SW2 and SW3) to provide a shorted path for the unwanted energy of the storage capacitor. A method for controlling such an internal energy dump is described in previously co-pending and commonly assigned U.S. application Ser. No. 08/811,834, now U.S. Pat. No. 5,873,893, entitled "METHOD AND APPARATUS FOR VERIFYING THE INTEGRITY OF AN OUTPUT CIRCUIT BEFORE AND DURING APPLICATION OF A DEFIBRILLATION PULSE", which is hereby incorporated by reference. In that application, it is described that by using the combination of switches SW2 and SW3 to discharge energy from the storage capacitor, a selected level of energy may be discharged. This may be accomplished because switch SW2 is an IGBT pair that can be made non-conducting, thus allowing the shorted path through the combination of switches SW2 and SW3 to be switched off once the selected amount of energy has been discharged.

Thus, the use of two legs on one side of the H-bridge circuit to discharge the capacitor eliminates the need for an additional internal energy dump circuit that is commonly used in the prior art. The prior art internal energy dump circuits have usually required the use of a resistor to absorb energy during the internal dump, in addition to the resistor that is used in the defibrillator to limit current during a defibrillation pulse. The internal energy dump resistors were often large (on the order of 100 kohms or more) so as to limit the current that would result in the internal dump circuitry.

In general, it was impractical to build internal dump circuitry with small resistors, because the resulting high currents would require relatively expensive and complex switching mechanisms, such as those used in FIG. 2, that are only justified in FIG. 2 by their function as part of the critical defibrillation circuit path. The large resistors of the prior art internal dump circuitry tended to cause the internal dump function to take several or more seconds to perform. For example, a 100 kohm resistor used with a 200 microfarad capacitor to reduce the energy level on the capacitor from 360 joules to 2 joules (as was required in the above example) would take more than several seconds to achieve. As described above, delays in defibrillator operation can put a patient at serious risk.

In contrast, the use of two of the legs of the H-bridge circuit allows the resistive component of the H-bridge that is used to limit current during a defibrillation pulse to also be used during the internal dump function. This resistive component is selected to have a value of less than 100 ohms which allows an internal dump such as that described above to be performed in less than one second. In fact, in an actual embodiment of FIG. 2, the protective component 27 has a resistive value of only 5 ohms and an inductive value of 840 uH. With an energy storage capacitor of 200 microfarads, this provides for approximately a one millisecond time constant, which allows an energy dump such as that described above to be performed in significantly less than one second. In addition, the protective component 27 is selected to have a high thermal capacity so that it can withstand the heat produced by the high currents that result during such an internal energy dump operation.

It will be appreciated that the greatest advantage of the output circuit 14 described above is that it allows an external defibrillator to generate and apply a high-energy biphasic waveform to a patient. For prior defibrillators providing a monophasic waveform, the standard energy level in the industry for the discharge has been greater than 200 joules. The above described circuit allows the same amount of energy (more than 200 joules) to be delivered to the patient in a biphasic waveform, thereby resulting in a greater certainty of defibrillation effectiveness for a broader range of patients. At the same time, the circuit incorporates special driving circuitry to allow even very low energy biphasic waveforms (less than 50 joules) to be delivered to the patient.

While the preferred embodiment of the invention has been illustrated and described, it will be apparent that various changes can be made therein without departing from the spirit and scope of the invention. For example, control lines 42c and 42d and control switches SW31 and SW41 could be replaced by a single control line and control switch to activate switch driving circuits 53 and 54. Also, while the preferred construction for switches 31, 32, 33, and 34 is described above, it will be appreciated that other switch constructions may be envisioned, such as replacing switch 32 with a single IGBT of sufficient stand-off voltage. Or, additional semiconductor switches may be incorporated in each leg to reduce the voltage that must be switched by each switch. To minimize the size and weight of the resulting output circuit 14, however, the construction described above is preferable. Consequently, within the scope of the appended claims, it will be appreciated that the invention can be practiced otherwise than as specifically described herein.

Figure 3:
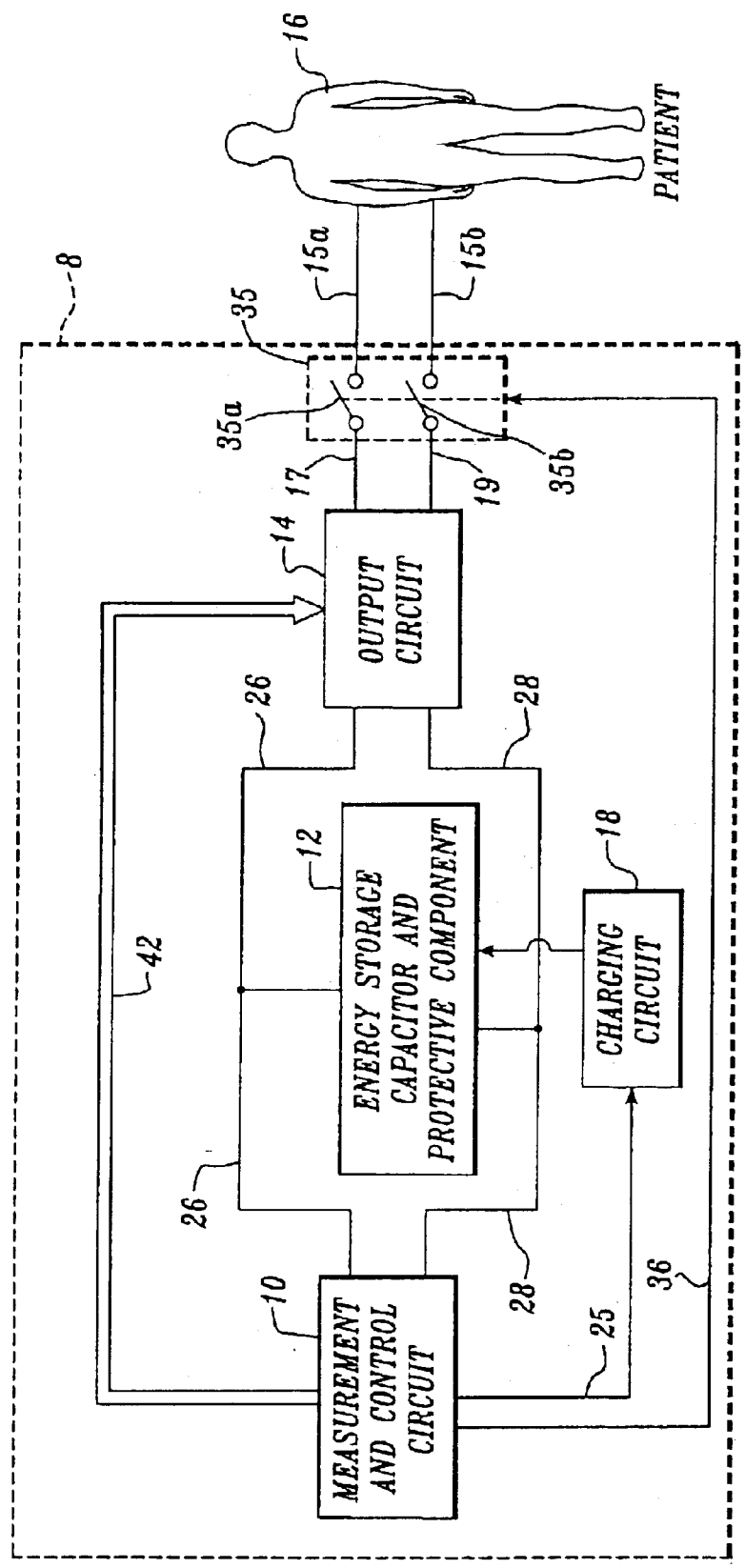
FIG. 3 is a block diagram of an external defibrillator having an output circuit that is tested before and during an application pulse in accordance with the present invention.
Figure 4:
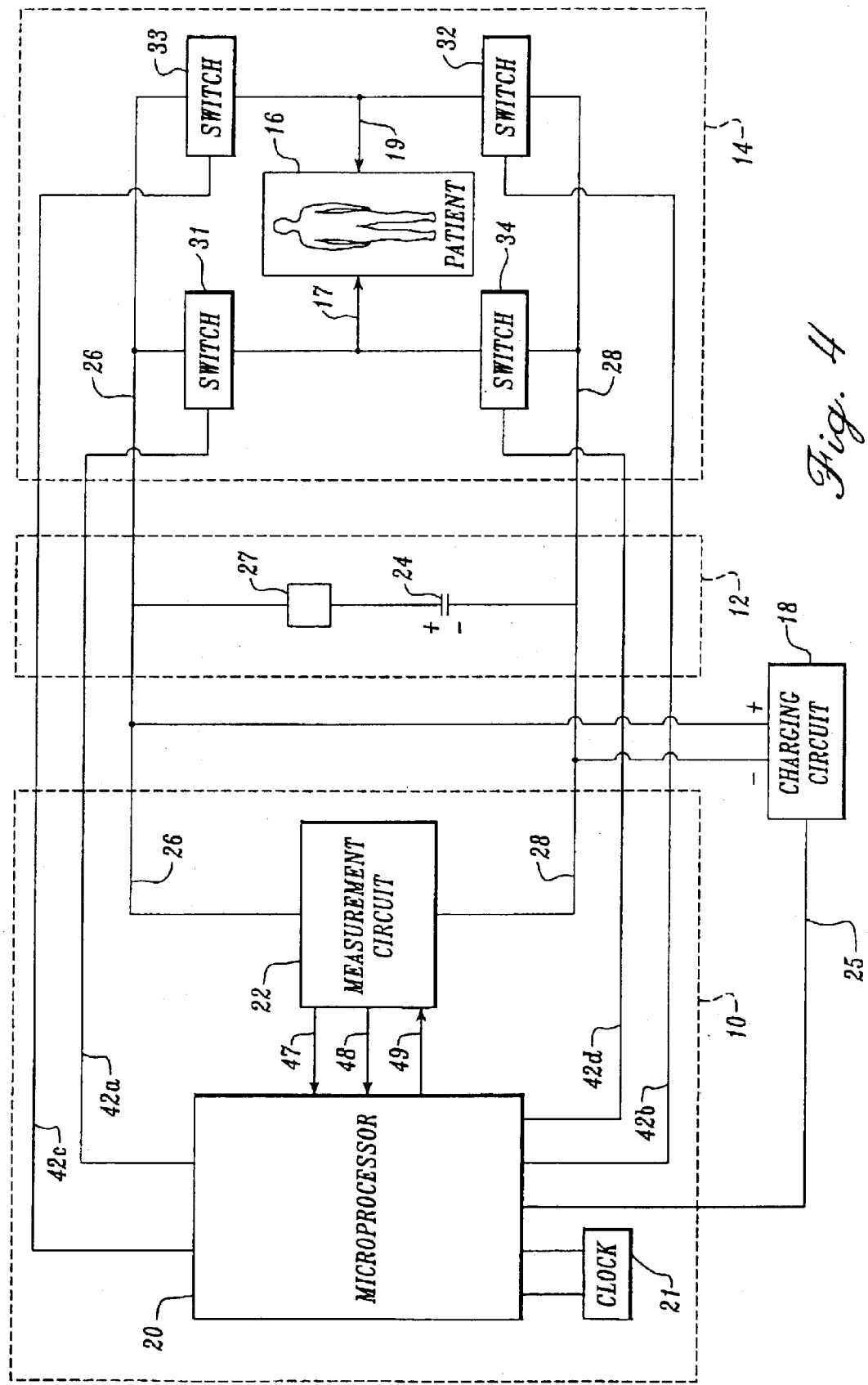
FIG. 4 is a block diagram of the external defibrillator of FIG. 3 depicting the construction of the output circuit and the connection of the output circuit to a scaling circuit.
Figure 5:
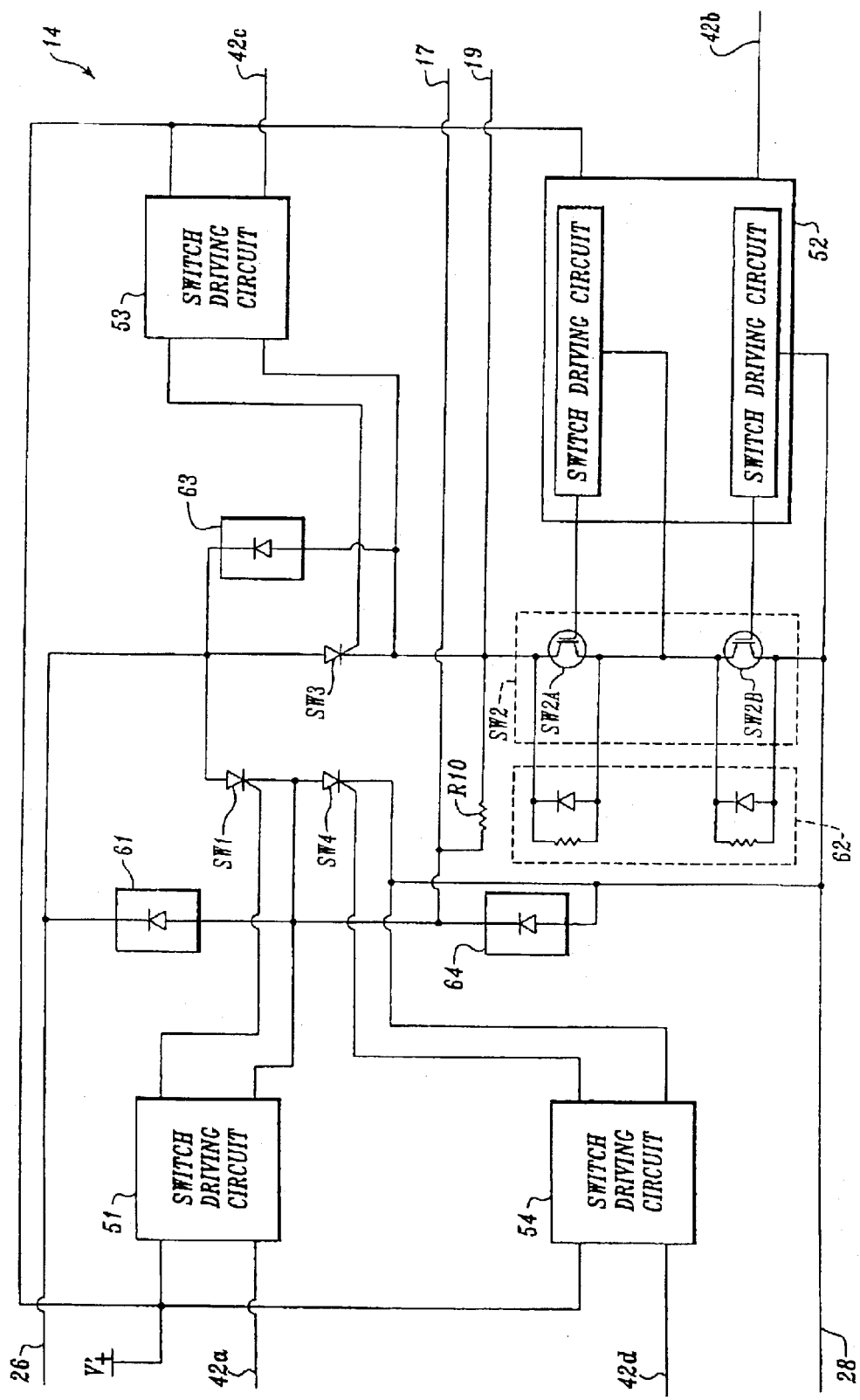
FIG. 5 is a schematic diagram of an actual embodiment of the output circuit of FIG. 2.

FIG. 3 is a block diagram of an external defibrillator 8 that is connected to a patient 16. FIGS. 3 to 5 are similar to FIG. 1, and include many of the same part designations. The defibrillator includes a measurement and control circuit 10 that is connected to an energy storage capacitor and protective component 12 via a charging circuit 18. During the operation of the defibrillator, the measurement and control circuit 10 controls the charging circuit 18 via a control line 25 to charge the energy storage capacitor to a desired voltage level. Feedback on the voltage level of the energy storage capacitor is provided to the measurement and control circuit 10 on a pair of lines 28 and 30.

After charging to a desired level, the energy stored in the energy storage capacitor may be delivered to the patient 16 in the form of a defibrillation pulse. The energy storage capacitor and protective component 12 is connected by lines 26 and 28 to an output circuit 14. The measurement and control circuit 10 is connected to the output circuit 14 by a control bus 42 and to a patient isolation relay 35 by a control line 36. Application of appropriate control signals over the control bus 42 and control line 36 causes the output circuit 14 to conduct energy from the energy storage capacitor. The energy is delivered to the patient 16 attached to the defibrillator 8 over a set of electrodes 15a and 15b. The electrode 15a is attached to an apex line 17 in output circuit 14 through a switch 35a in the patient isolation relay. The electrode 15b is attached to a sternum line 19 in output circuit 14 through a switch 35b in the patient isolation relay. In a manner described in greater detail below, the measurement and control circuit 10 verifies the integrity of the output circuit 14 before and during the transfer of the defibrillation pulse.

The components of the defibrillator 8 are depicted in greater detail in FIG. 4. A microprocessor 20, scaling circuit 22, and charging circuit 18 are used to charge an energy storage capacitor 24 to a desired voltage. To control the charging, the microprocessor 20 is connected to the scaling circuit 22 by a pair of measurement lines 47 and 48, and by a control line 49. The microprocessor is also connected to the charging circuit 18 by a control line 25. The scaling circuit 22 and charging circuit 18 are connected to the energy storage capacitor 24 by a bridge line 28, which connects to the negative lead of the capacitor, and by a line 30, which connects to the positive lead of the capacitor. A clock 21 is also connected to the microprocessor 20.

Figure 6:
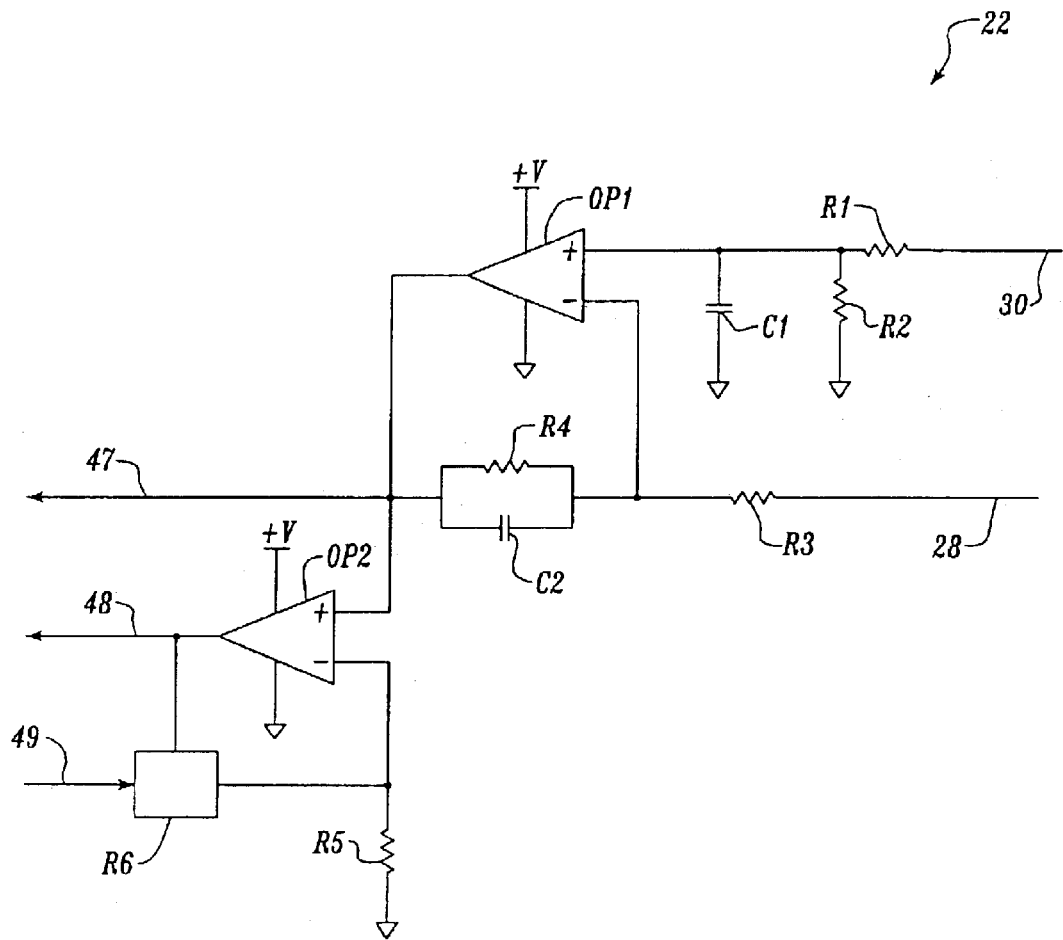
FIG. 6 is a schematic diagram of an actual embodiment of the scaling circuit of FIG. 2.

The scaling circuit 22 is used to monitor the voltage across the energy storage capacitor 24. FIG. 6 is a circuit diagram of an actual embodiment of the scaling circuit 22. The scaling circuit 22 steps down the voltage level across the energy storage capacitor 24 to a range that can be measured by the microprocessor 20 on measurement lines 47 and 48. The scaling circuit 22 includes two operational amplifiers OP1 and OP2. A resistor R1 is connected between line 30 and the non-inverting input of operational amplifier OP1, and a resistor R2 and a capacitor C1 are connected in parallel between the non-inverting input of operational amplifier OP1 and ground. A resistor R3 is connected between the inverting input of operational amplifier OP1 and bridge line 28. A resistor R4 and a capacitor C2 are connected in parallel between the inverting input of operational amplifier OP1 and the output of operational amplifier OP1. The output of operational amplifier OP1 is connected to the non-inverting input of operational amplifier OP2 and to measurement line 47.

The DC voltage level of the energy storage capacitor 24 is stepped down for application to the operational amplifier OPI. The ratio of resistors R1 and R3 to resistors R2 and R4 is generally very high so as to significantly step down the voltage at this stage. The values of resistors R1 and R3 are also typically very high, so as to limit the current drain from the capacitor 24. The capacitors C1 and C2 are provided to filter out high-frequency voltage spikes. In an actual embodiment of the scaling circuit 22, the scaling circuit will step down a voltage of 2200V across the energy storage capacitor 24 to less than 5V on measurement line 47. The microprocessor 20 is provided with a 5V analog-to-digital converter to measure the voltage on the measurement line 47 and monitor the voltage across the energy storage capacitor 24.

If the energy storage capacitor 24 was always charged to 2200V, the scaling circuit described thus far would be adequate. In the preferred embodiment, however, the energy storage capacitor 24 can be charged to a range of voltage levels with the selected level depending on the patient and other parameters. The range to which the energy storage capacitor 24 may be charged in the preferred embodiment is from 100V to 2200V. To detect small percentage changes in the selected voltage level of the energy storage capacitor 24, the scaling circuit is therefore adjustable to account for different voltage ranges.

To account for the range of the input voltages into the scaling circuit 22, the non-inverting input of operational amplifier OP2 is connected to the output of operational amplifier OP1. A resistor R5 is connected between the inverting input of operational amplifier OP2 and ground. A digital variable gain pot R6 is connected between the inverting input of operational amplifier OP2 and the output of operational amplifier OP2. The digital variable gain pot R6 is controlled by a signal received on the control line 49 connected to the microprocessor 20. The output of operational amplifier OP2 is connected to measurement line 48. The gain provided by operational amplifier OP2 is adjustable by varying the setting of the digital variable gain pot R6.

The gain of the operational amplifier OP2 is set by the microprocessor 20. A measurement is initially made of the voltage on measurement line 47 which, as described above, in the actual embodiment ranges from 0 to approximately 5V. Based on the measured voltage, the gain of operational amplifier OP2 is adjusted to make the voltage on measurement line 48 close to 5V. Adjusting the output to nearly 5V allows the full range of precision of the 5V analog-to-digital converter in the microprocessor to be used. The microprocessor 20 uses the known gain of amplifiers OP1 and OP2 in conjunction with the output voltage provided on measurement line 48 to measure the energy storage capacitor 24 voltage level. As will be described in more detail below, changes in the energy storage capacitor voltage level are used to verify the integrity of the output circuit 14.

Returning to FIG. 4, the output circuit 14 allows the controlled transfer of energy from the energy storage capacitor 24 to the patient 16. The output circuit 14 includes four switches 31, 32, 33, and 34, each switch forming one leg of the H-bridge. Switches 31 and 33 are coupled through a protective component 27 to the positive lead of the energy storage capacitor 24 by bridge line 26. The protective component 27 has both inductive and resistive properties to limit the current and voltage changes from the energy storage capacitor 24. Switches 32 and 34 are coupled to the negative lead of the energy storage capacitor 24 by bridge line 28. The center cross line of the H-bridge includes the patient 16, which is connected to the left side of the bridge by an apex line 17, and to the right side of the bridge by a sternum line 19. Although omitted for clarity in FIG. 4, the apex line 17 and the sternum line 19 are connected to the electrodes 15a and 15b by the patient isolation relay 35. The microprocessor 20 is connected to the switches 31, 32, 33, and 34 by control lines 42a, 42b, 42c, 42d, respectively, and to the patient isolation relay 35 by control line 36, allowing the switches and relay to be opened and closed under microprocessor control. Control lines 42a, 42b, 42c, and 42d are part of the control bus 42.

An actual embodiment of the output circuit 14 is shown in FIG. 5. The circuit diagram of FIG. 5 is described briefly below, and a more detailed embodiment is described above with reference to FIG. 2. As shown in FIG. 5, four output switches SW1 to SW4 allow the transfer of energy from the energy storage capacitor on lines 26 and 28. Switches SW1, SW3, and SW4 are semiconductor switches, preferably silicon controlled rectifiers (SCRs). Switch SW2 is a series combination of switches SW2A and SW2B, which are both insulated gate bipolar transistors (IGBTs). The four output switches SW1 to SW4 can be switched from an off (non-conducting) to an on (conducting) condition. Control lines 42a, 42b, 42c, and 42d are connected to switch driving circuits 51, 52, 53, and 54, which are connected to switches SW1 to SW4, respectively. Switch driving circuit 52 contains two identical switch driving circuits, each circuit corresponding to one of the IGBTs.

The switch driving circuits 51, 53 and 54 switch the respective SCR switches on or off according to signals on control lines 42a, 42c, and 42d. Switches SW1, SW3, and SW4 remain conducting as long as the signal on the corresponding control line is present. Each switch SW1 to SW4 is also connected to a switch protection circuit 61, 62, 63, and 64, respectively. Switch driving circuit 52 switches the IGBT switches on or off according to a signal on control line 42b. As long as the signal on control line 42b is present, switch SW2 will remain conducting. Switch protection circuit 62 contains two identical switch protection circuits, each protection circuit corresponding to one of the IGBTs. Switch protection circuits 61, 62, 63, and 64 protect the switches SW1 to SW4 from being damaged by reverse voltages, and from conducting prematurely.

In the preferred embodiment, the defibrillator 8 provides a biphasic defibrillation pulse to the patient in the following manner. With reference to FIG. 5, once the energy storage capacitor 24 is charged to a selected energy level and the patient isolation relay 35 is closed, the switches SW1 and SW2 are switched on so as to provide a path from the energy storage capacitor to apex line 17 and sternum line 19, respectively, for the application of a first phase of a defibrillation pulse to the patient. The stored energy travels from the positive terminal of the capacitor 24 on line 26, through switch SW1, across apex line 17, across the patient 16, back across sternum line 19, and through switch SW2 to the negative terminal of the capacitor 24 on line 28. The first phase of the biphasic pulse therefore applies a positive pulse from the apex to the sternum of the patient.

Before the energy storage capacitor 24 is completely discharged, switch SW2 is biased off in preparation for applying the second phase of the biphasic pulse. Once switch SW2 is biased off, switch SW1 will also become non-conducting because the voltage across the SCR falls to zero.

After the end of the first phase of the biphasic defibrillation pulse, the switches SW3 and SW4 are switched on to start the second phase of the biphasic pulse. Switches SW3 and SW4 provide a path to apply a negative defibrillation pulse to the patient. With reference to FIG. 5, the energy travels from the positive terminal of the capacitor 24 on line 26, through switch SW3, across sternum line 19, through the patient 16, back across apex line 17, and out through switch SW4 to the negative terminal of the capacitor 24 on line 28.

The polarity of the second phase of the defibrillation pulse is therefore opposite in polarity to the first phase of the pulse. The end of the second phase of the biphasic pulse is truncated by switching on switch SW1 to provide a shorted path for the remainder of the capacitor energy through switches SW1 and SW4. After the second phase is truncated, all four of the switches SW1 to SW4 are switched off. The patient isolation relay 35 is also opened to allow the energy storage capacitor 24 to be recharged in preparation for providing another defibrillation pulse.

Figure 7A:
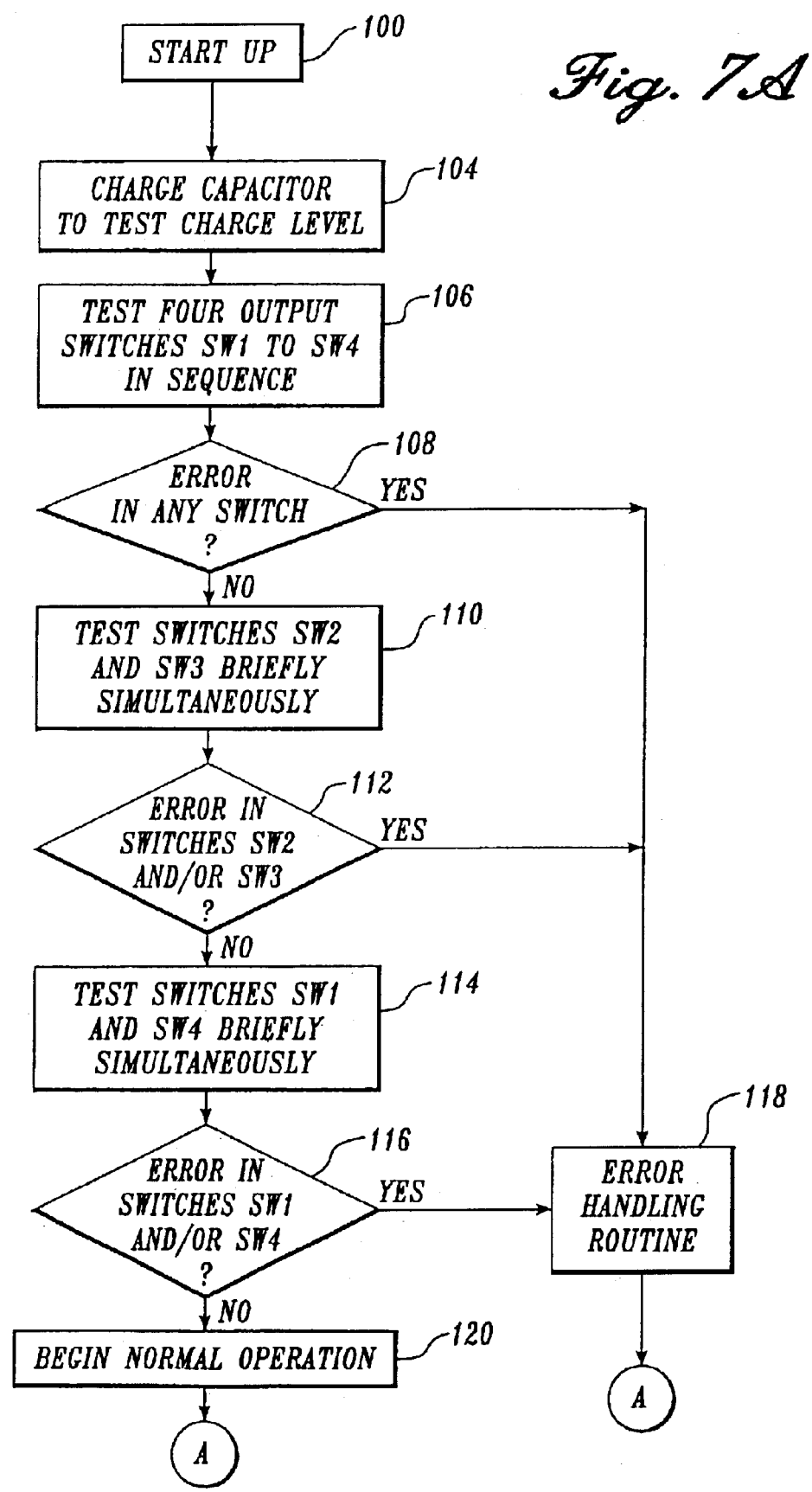
FIGS. 7A–7B are flow charts of an exemplary routine for testing the output circuit prior to and during the delivery of a defibrillation pulse to a patient.

The integrity of the output circuit 14 is verified prior to and during the delivery of a defibrillation pulse. A preferred method of verifying the integrity of the output circuit 14 is illustrated in the flow charts of FIGS. 7A–7B. FIG. 7A depicts a start-up verification test performed after the defibrillator is turned on and prior to delivery of a defibrillation pulse. After turning on the defibrillator at a block 100, the energy storage capacitor is charged to a test voltage at a block 104. The test voltage to which the energy storage capacitor is charged may be less than the maximum allowed voltage of the capacitor if energy conservation during the start-up test is desired. A lower voltage requires less charging time, and therefore allows the total start-up test time of the output circuit to be shortened. The test voltage should be high enough, however, to allow a reasonable test of the integrity of the output switches SW1 to SW4, as set forth below. During the entirety of the start-up verification test of the output circuit, it will be appreciated that the patient isolation relay 35 is opened to prevent any current from flowing to a patient.

After charging the energy storage capacitor, at a block 106 a sequential test is made of the four output switches SW1 to SW4. The output switches are initially tested by switching the switches off. After placing each of the switches in the non-conducting state, each switch is individually switched on and then off again in sequence. That is, the first switch SW1 is switched on and then off, followed by the remaining switches in turn. As the switches are being switched on and off, the voltage level across the energy storage capacitor is monitored. No change in the voltage level across the energy storage capacitor 24 should occur during the tests, because switching on a single switch does not provide a conductive path through the output circuit 14 that would allow the energy stored in the energy storage capacitor to discharge. If any change in the voltage level across the capacitor during the sequential switching on and off of switches SW1 to SW4 is detected, an error is indicated. At a block 108, a test is made to determine whether there were errors detected in any of the switches SW1 to SW4. If any errors were detected in the switches, at a block 118 an error handling routine is called. The error handling routine will be described in additional detail below. If no errors were detected in the switches, the start-up verification test proceeds to a block 110.

At block 110 the switches SW2 and SW3 are tested simultaneously for a brief interval. The two switches are tested by simultaneously switching on both switch SW2 and SW3. The switches are turned off by biasing switch SW2 off, which causes switch SW3 to become non-conducting since it is an SCR. When switches SW2 and SW3 are simultaneously conducting, a drop in the voltage across the energy storage capacitor should be detected due to the shorted path that is provided through the output circuit 14. If a voltage drop is not detected when switches SW2 and SW3 are supposed to be simultaneously conducting, then an error is indicated. At a block 112, a test is made to determine whether an error was detected in the combination of switches SW2 and SW3. If an error was detected, the start-up verification test continues to the error handling routine at block 118. If no error was detected in switches SW2 and SW3, the start-up test continues to a block 114.

At block 114, a test is made of switches SW1 and SW4. Switches SW1 and SW4 are tested by simultaneously switching the switches on. Switching on switches SW1 and SW4 causes a conductive path to be created from the energy storage capacitor 24 through the output circuit 14. A voltage drop across the energy storage capacitor should therefore be detected. If a voltage drop is not detected when switches SW1 and SW4 are simultaneously switched on, then an error is indicated. At block 116, a test is made to determine whether an error was detected in the combination of switches SW1 and SW4. If an error was detected, the start-up verification test continues to the error handling routine at block 118. If no error was detected in switches SW1 and SW4, the start-up test continues to block 120 where the defibrillator enters normal operation.

It will be appreciated that in the embodiment of the output circuit 14 shown in FIG. 5, the set of switches SW2 and SW3 must be tested before the set of switches SW1 and SW4. If switches SW1 and SW4 had been tested first, it would have been impossible to switch the switches SW1 and SW4 off while current was flowing through them because they are both SCR devices. Testing switches SW1 and SW4 first would therefore have drained all the test energy from the energy storage capacitor 24. Because switch SW2 is an IGBT pair that can be made non-conducting, the combination of switches SW2 and SW3 can be switched off. Testing the switches in the correct order therefore allows the energy storage capacitor to be charged a single time in order to test all four switches. It will be appreciated, however, that a different switch testing order could be used if the capacitor were recharged or if different switches were used in the output circuit.

The start-up verification test is performed immediately after turning the defibrillator on because it requires extra time and energy to charge and then dissipate the energy in the energy storage capacitor. The amount of time and energy that the start-up tests takes can be varied by changing the voltage level to which the energy storage capacitor is charged. Using a lower voltage level reduces the charge time of the capacitor. In an alternate embodiment, a "skip start-up test" button or command may also be incorporated in the defibrillator to allow a user to bypass the start-up verification test as the defibrillator is powered on.

In addition to being performed when a user powers on the defibrillator, in an alternate embodiment the start-up verification test may also be performed periodically by the microprocessor 20 while the defibrillator is not in use. For example, at a certain time each night as shown by clock 21, the microprocessor 20 could automatically and without user intervention power on the defibrillator, perform tests to verify the integrity of the output circuit, and, as described below with respect to the error handling routine, provide a warning signal to a user if a failure has occurred.

Figure 7B:
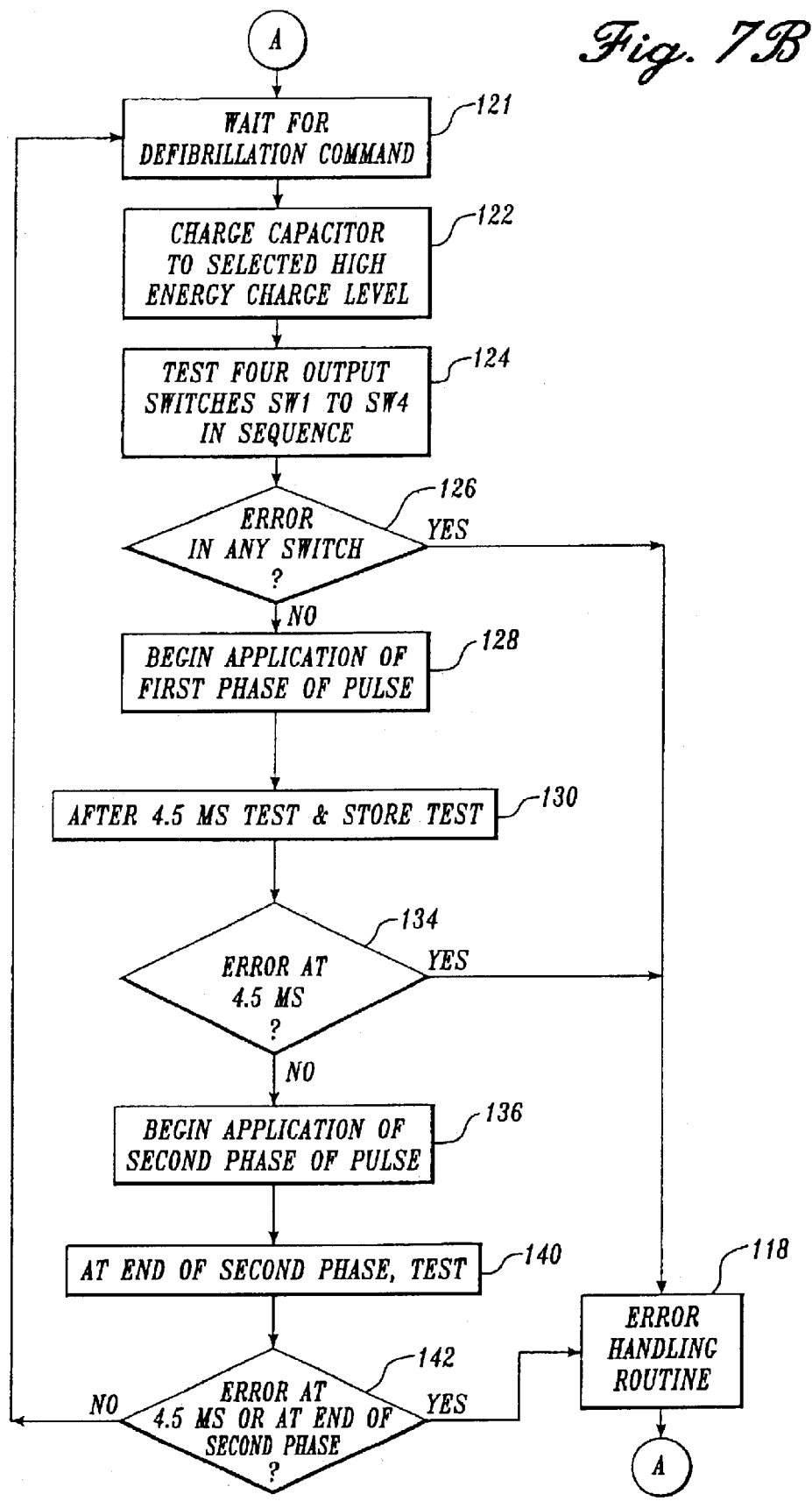

FIG. 7B depicts the verification tests performed immediately prior to, and during the delivery of, a defibrillation pulse. After entering the normal mode of operation, at a decision block 121 the defibrillator waits to receive a command indicating that a defibrillation pulse is to be applied to a patient. If implemented in an automatic defibrillator, the command will be generated by the microprocessor after analysis of an electrocardiogram from the patient. Alternatively, in a manual defibrillator, the command to charge the energy storage capacitor for application of a defibrillation pulse may come from trained medical personnel using the device.

If a command is received indicating that the defibrillator should prepare to apply a defibrillation pulse to a patient, the verification test proceeds to a block 122. At block 122 the energy storage capacitor 24 is charged to a selected voltage. Several factors determine the charge level of the capacitor, including the selected energy level that is to be delivered to the patient.

After charging the capacitor to the desired voltage, at a block 124 a test is made of the four output switches SW1 to SW4. The test is identical to the test performed at block 106. That is, each of the switches are individually switched on and then off. While the switches are switched on and off, the voltage across the energy storage capacitor is monitored by the microprocessor. If all the switches are operational (i.e., none of the switches are stuck in a conducting state), the voltage across the energy storage capacitor should not change during the testing. The verification test performed at block 124 is capable of being performed prior to delivery of the defibrillation pulse because the test can be performed quickly and with no energy loss from the energy storage capacitor if no faults occur. If a faulty switch is identified that is stuck in a conducting state prior to delivery of the defibrillation pulse, the verification test can discover the error before the defibrillator attempts to deliver the defibrillation pulse to the patient.

After testing each of the switches, at a block 126 a test is made to determine if there were any errors detected in any of the switches. If any errors were detected, then at block 118 the error handling routine is called. If no errors were detected in the switches, the defibrillator may deliver the defibrillation pulse to the patient. The patient isolation relay 35 is closed prior to the delivery of the defibrillation pulse.

At a block 128, switches SW1 and SW2 are switched on to start the application of the first phase of the defibrillation pulse. As the first phase of the pulse is being delivered to the patient, a clock is started. After a predetermined time from the start of the first phase, preferably 4.5 milliseconds, the microprocessor measures the voltage on the energy storage capacitor at a block 130. After 4.5 milliseconds, the voltage level of the capacitor should have dropped to within a certain range that is defined based on the known range of patient impedances. If the measured voltage level across the energy storage capacitor is not within the expected range after 4.5 milliseconds, then a failure is present in either the output circuit or the connection to the patient. At a decision block 134, a test is made to determine if a failure was detected at 4.5 milliseconds. If a failure was detected, an error handling routine is called at block 118. If a failure was not indicated during delivery of the first phase, then the second phase of the biphasic defibrillation pulse may be applied to the patient. Prior to starting the second phase, switch SW2 is switched off to truncate the application of the first phase.

At a block 136, switches SW3 and SW4 are switched on to provide a conductive path from the energy storage capacitor to the patient and begin the application of the negative second phase of the defibrillation pulse. At a block 140, a measurement is made of the voltage across the capacitor at the end of the second phase. The measured voltage at the end of the second phase should fall within a certain range based on the expected patient impedances. If the measured voltage falls outside the expected range, a failure of the output circuit or the connection to the patient is indicated.

At a decision block 142, a test is made to determine if a failure was indicated at the end of the second phase. If a failure was indicated, the verification test proceeds to the error handling routine at block 118. If no failure was indicated, the verification test returns to decision block 121 to wait to receive another command to charge the energy storage capacitor for delivery of an additional defibrillation pulse. After the end of the second phase, the patient isolation relay 35 is opened to isolate the patient from the defibrillator.

It will be appreciated that while the 4.5 millisecond test performed at block 130 was only performed during the first phase of the defibrillation pulse, a similar test could have been performed 4.5 milliseconds after the start of the second phase. Similarly, while the test of the ending voltage performed at block 140 was only performed at the end of the second phase, a similar test could have been performed at the end of the first phase.

The testing method disclosed herein is advantageous in that it allows the integrity of the output circuit and connection to the patient to be checked both before and during the application of the defibrillation pulse. Many prior defibrillators were unable to perform such testing due to the type of output switch and the EMI noise generated by the application of a defibrillation pulse. If any error is detected before or during delivery of the defibrillation pulse, an error handling routine may be called to analyze and compensate for the indicated failure.

Figure 8A:
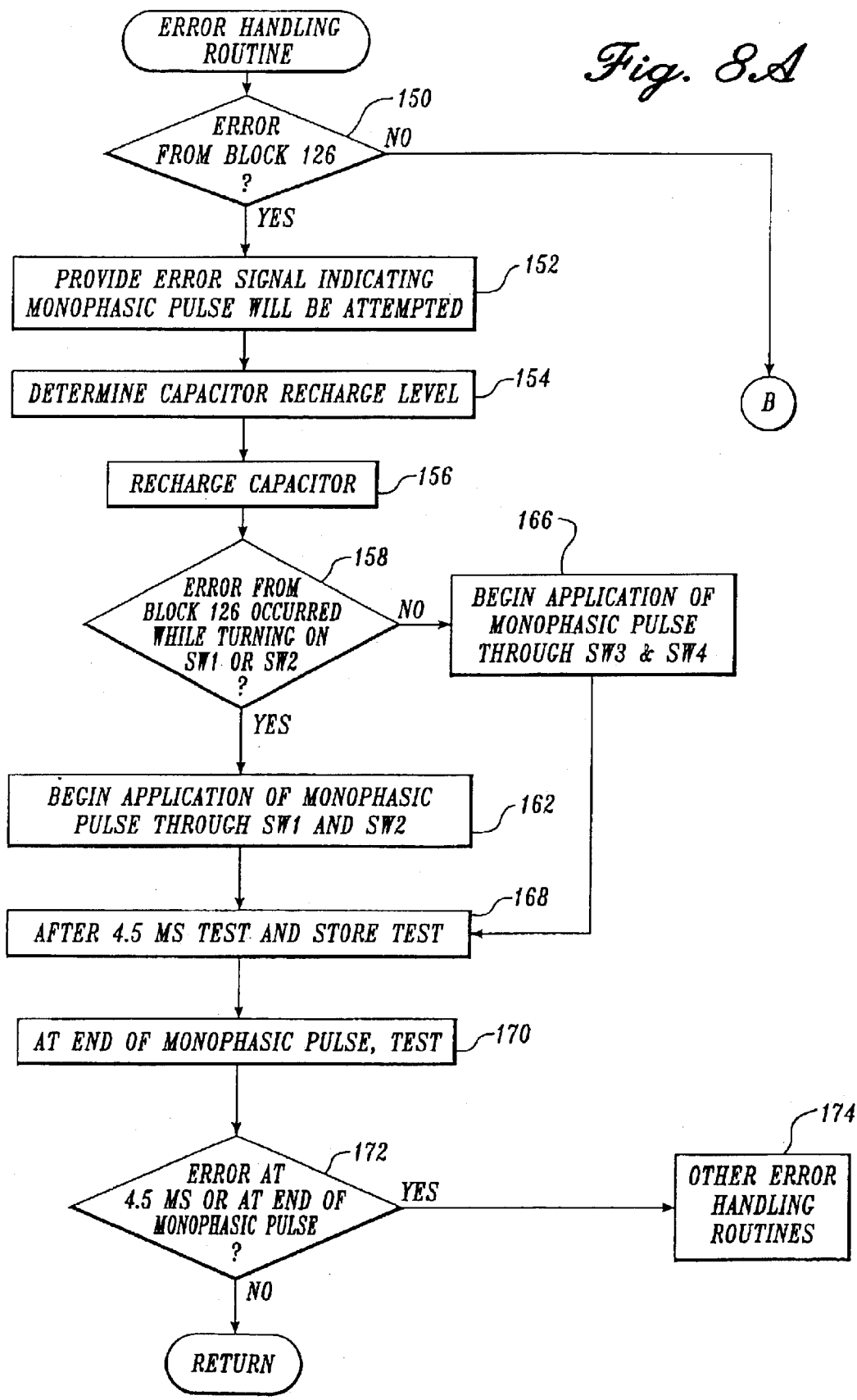
FIGS. 8A–8B are flow charts of an exemplary error handling routine for analyzing and compensating for particular errors should an error be detected while testing the output circuit.
Figure 8B:
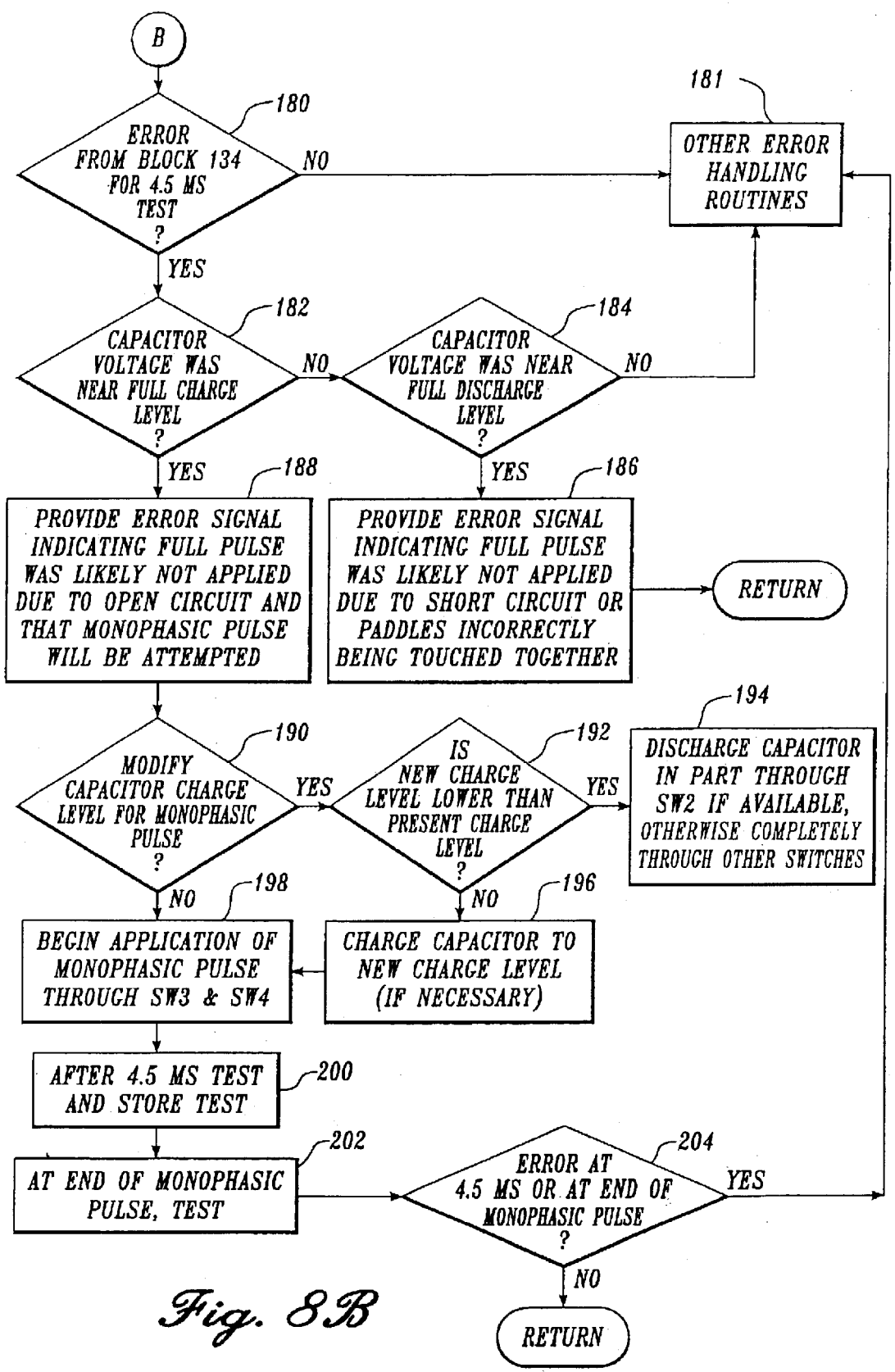

When an error is indicated before or during delivery of a defibrillation pulse, the error handling routine is called at block 118. The error handling routine may perform several types of analyses to further determine the cause of the error. If possible, the error handling routine may also compensate for the error by applying a monophasic, rather than a biphasic, pulse to the patient. FIGS. 8A and 8B are flow charts of a representative error handling routine.

If one of the switches in the output circuit is stuck in the conducting state, the defibrillator may compensate for the stuck switch by using the available conducting switching path to deliver a monophasic, rather than a biphasic, pulse. FIG. 8A illustrates the application of a monophasic pulse if the failure of a switch is detected prior to a defibrillation pulse being applied. At a block 150, a test is made to determine if the error handling routine was entered from block 126. If the error handling routine was not entered from block 126, the routine proceeds to a block 180. If the error handling routine was entered from block 126, the routine proceeds to a block 152.

At block 152, an error signal is provided to the user to indicate that an error has occurred and that a monophasic pulse will be attempted. The error signal may be an audible, visual, and/or logged alarm. At a block 154, a determination is made as to whether the current charge level of the energy storage capacitor is sufficient to generate a desired monophasic pulse. It will be appreciated that the size of a desired monophasic pulse may be varied depending on the impedance of the patient, the number of shocks previously applied to the patient, and other factors. To change the duration and magnitude of the monophasic pulse, the energy storage capacitor 24 charge level is modified. If the monophasic pulse is to have a higher current or longer duration than the pulse that would be delivered based on the current charge level on the capacitor, the energy storage capacitor is charged to a higher voltage. Conversely, if the monophasic pulse is to have a lower current or shorter duration, the voltage on the capacitor is reduced. To reduce the voltage, the capacitor 24 can be discharged in part through a shorted path provided by closing both output switches on one side of the H-bridge output circuit 14. At a block 156, the energy storage capacitor 24 is charged to the selected level. The patient isolation relay 35 is also closed to prepare for the application of the monophasic pulse.

At a block 158, a test is made to determine the specific output switch that is stuck in a conducting state. If during the tests at blocks 106 or 124 a shorted conducting path is formed so that the voltage on the capacitor 24 changes rapidly when only switch SW1 is switched on, then it is logical to infer that either switch SW4 is stuck in a conducting state or else that there is a short somewhere in the system. This logic follows because of the three remaining switches when switch SW1 is supposed to be conducting, only switch SW4 being conductive should cause a shorted conductive path to be formed. Similarly, a rapid voltage change when only switch SW2 is switched on may indicate that switch SW3 is stuck in a conducting state, and vice versa. An error detected while switch SW1 or SW2 is switched on may therefore indicate that switch SW4 or SW3, respectively, is stuck in a conducting state and vice versa. If the error was indicated in switches SW1 or SW2, the error routine proceeds to a block 162 where it begins the application of the monophasic pulse through switches SW1 and SW2. Switches SW1 and SW2 are required to be used in this circumstance because if one of them is stuck in a conducting state, then switches SW1 and SW2 provide the only effective defibrillation path. Similarly, if the error was indicated in switches SW3 or SW4, the routine proceeds to a block 166 where it begins the application of the monophasic pulse through switches SW3 and SW4.

From either block 162 or block 166, the routine proceeds to a block 168, where a measurement is made of the voltage across the energy storage capacitor at a predetermined time after the start of the monophasic pulse. Preferably, the voltage measurement is made at 4.5 milliseconds. The rate of decay of the monophasic pulse is dependent on a known range of patient impedances. After 4.5 milliseconds, the measured voltage across the energy storage capacitor should therefore fall within an expected range. If the voltage across the energy storage capacitor falls outside the expected range, a failure of the output circuit or of the connection to the patient is indicated.

At a block 170, a measurement is made of the voltage across the capacitor at the end of the monophasic pulse. The measured voltage at the end of the monophasic pulse should fall within a certain range based on the expected patient impedances. If the measured voltage falls outside the range, a failure of the output circuit or of the connection to the patient is indicated.

At a decision block 172, a test is made to determine if a failure was indicated at either 4.5 milliseconds or at the end of the monophasic pulse. If a failure was indicated, the routine proceeds to other error handling routines at block 174. If no failure was indicated, the routine returns to block 121 to wait for another defibrillation command, under the theory that the original error condition identified in block 126 may have been merely a transient condition. In an alternate embodiment, rather than proceeding back to block 121, the routine may proceed to a block which again applies a monophasic pulse when the next defibrillation command is given.

FIG. 8B illustrates the analysis and attempted compensation that occurs if an error is detected during the application of a biphasic defibrillation pulse. At a block 180, a test is made to determine if the error handling routine was entered from block 134 due to an error that was detected 4.5 milliseconds after the start of the first phase of the defibrillation pulse. If the routine was not called from block 134, the routine proceeds to a block 181 where other error handling routines are called. If the routine was initially called from block 134, the routine proceeds to a block 182.

At block 182 a test is made to determine if the energy storage capacitor voltage that was measured at block 130 is above the expected range and near the fully charged level. If the voltage is not near the fully charged level, the routine proceeds to a block 184. At block 184 a test is made to determine if the energy storage capacitor voltage that was measured at block 130 is near the fully discharged level. If the voltage is not near the fully discharged level, the routine proceeds to a block 181 where other error handling routines are called. If the voltage is near the fully discharged level, the routine proceeds to a block 186 where an error signal is provided to the user of the defibrillator indicating that the full defibrillation pulse was likely not applied to the patient. After block 186 the routine returns to block 121 to wait for another defibrillation command, under the theory that the original error identified in block 134 may have been a transient problem. The error signal provided at block 186 illustrates one aspect of the importance of the test performed during the application of a defibrillation pulse. Tests made after the pulse is over only indicate that the energy has been discharged, and do not indicate if the energy went through the patient or through a short circuit. Tests made during the defibrillation pulse, however, provide an accurate indication that the defibrillation pulse was applied to the patient.

Returning to block 182, if the voltage across the energy storage capacitor is near the fully charged level, the routine proceeds to a block 188. At block 188 an error signal is provided to the user indicating that the capacitor voltage is still near the full charge level and that a monophasic pulse will be attempted. A full charge on the capacitor likely indicates a switch failure or an open circuit within the defibrillator. At a block 190, a test, is made to determine if the charge level of the capacitor should be changed before the application of the monophasic pulse. As was described above, changing the charge level alters the current and duration of the monophasic pulse. The desired current and duration may be selected based on various parameters, including the impedance of the patient and whether the patient has been shocked before. If the charge level does not need modification, the routine proceeds to a block 198. If the charge level is to be modified, the routine proceeds to a block 192.

At block 192 a test is made to determine if the desired charge level is higher or lower than the present charge level. If the desired charge level is higher, the routine proceeds to a block 196. If the desired charge level is lower, the routine proceeds to a block 194 where an attempt is made to lower the charge level by switching on switches SW2 and SW3 to provide a shorted path across the capacitor. An attempt is made to use switches SW2 and SW3 first because, as described above, switch SW2 may be biased off before all of the energy of the storage capacitor is discharged. If switch SW2 is not available at block 194, switches SW1 and SW4 are switched on to discharge all the energy of the capacitor. After block 194 the routine proceeds to block 196.

At block 196, if necessary, the energy storage capacitor is charged to a new level. The routine then proceeds to block 198, where the monophasic pulse is applied by turning on switches SW3 and SW4. Switches SW1 and SW2 are not used for the application of the monophasic pulse because the routine was called when an open circuit error was indicated while attempting to provide a pulse through switches SW1 and SW2.

After 4.5 milliseconds of the monophasic pulse have elapsed, a measurement is made of the voltage across the energy storage capacitor at a block 200. At a block 202 a measurement of the voltage across the storage capacitor is made at the end of the monophasic pulse. If the voltage is outside the expected range for either test, a failure of the output circuit or of the connection to the patient is indicated.

At a decision block 204 a test is made to determine if a failure was indicated at either 4.5 milliseconds or at the end of the monophasic pulse. If a failure was indicated, the routine proceeds to other error handling routines at block 181. If no failure was indicated, the routine returns to block 121 to wait for another defibrillation command, under the theory that the original error condition in block 134 may have been cleared. In an alternate embodiment, rather than proceeding back to block 121, a monophasic pulse may be automatically applied when the next defibrillation command is given.

Providing a monophasic pulse if a portion of the output circuit should fail offers a distinct advantage over prior monophasic, including Edmark pulse, defibrillators. Generally, in prior monophasic defibrillators, there was only one active switching path, and if part of that path failed, the defibrillator became inoperable. In the present invention, the existence of two conductive paths through the H-bridge output circuit 14 provides a "backup" path that can be used for providing a monophasic pulse in the event that one of the paths fails.

The analysis depicted in FIGS. 8A and 8B is merely representative of some of the diagnostic tests that may be performed on the output circuit to analyze an error condition. Those skilled in the art will recognize that other tests could also be envisioned. For example, another possible type of analysis that the error handling routine may perform is locating a specific output switch that is stuck in a non-conducting state. If during the tests in block 110 a shorted path is not formed such that the voltage on the capacitor 24 does not quickly change when switches SW2 and SW3 are supposed to be conducting, then it is logical to infer that either switch SW2 or SW3, or both, is stuck in a non-conducting state, or else that there is an open circuit in the system. Similarly, a lack of rapid voltage change when switches SW1 and SW4 are supposed to be conducting in block 114 may indicate that either switch SW1 or SW4, or both, is stuck in a non-conducting state. Given this information alone, it cannot be determined exactly which of the two switches being tested is stuck, because if either or both of the two switches are stuck in a non-conducting state, the voltage will not change. Once it is determined that either or both of the switches may be stuck in a non-conducting state, however, appropriate error messages and instructions can be provided to the user and additional tests can be performed to specifically locate the faulty switch. One response that the defibrillator may invoke when such an error occurs and the faulty switch is specifically located is to deliver a monophasic rather than a biphasic pulse, using the switching path that is available for such a pulse, possibly with higher current or longer duration.

Another type of analysis that the error handling routine may perform is determining the cause of erroneous voltage readings that are measured at blocks 130 and 140. A measured voltage level that is too high may indicate that there is too much impedance, i.e., that the paddles or electrodes are not being properly applied to the patient. No voltage drop at all may indicate that one of the switches SW1 to SW4 is stuck in a non-conducting state. A specific output switch being stuck in a non-conducting state can be pinpointed by this test combined with the tests at blocks 110 and 114. A measured voltage level that is too low may indicate that a switch is stuck in a conducting state or that the electrodes have been touched together.

While the preferred embodiment of the invention has been illustrated and described, it will be apparent that various changes can be made therein without departing from the spirit and scope of the invention. For example, while the preferred embodiment contemplates using the output circuit to generate a biphasic defibrillation pulse to a patient, the output circuit may also be used to generate a multiphasic defibrillation pulse with three or more phases.

It will also be appreciated that while the voltage across the energy storage capacitor was the measured parameter for the tests performed in FIGS. 7A to 7B, any parameter that is related to the energy flow from the capacitor to the patient may be used to estimate the impedance of the discharge. For example, the current of the discharge, the time of the discharge, or the voltage/current ratio could all be compared against expected ranges that are defined based on the known range of patient impedances. Any measured parameter that was not within the expected range could indicate a failure in the output circuit.

Moreover, while a microprocessor 20 is used in the preferred embodiment to control testing and analysis of the output circuit 14, it will be appreciated that other controllers could be used to perform the same task. For example, an ASIC or discrete logic could be used to govern the testing. It will also be appreciated that while a single energy storage capacitor 24 is depicted herein, other energy storage devices could be envisioned. For example, multiple capacitors could be coupled to store the desired amount of energy.

It will further be appreciated that while switches SW1, SW3 and SW4 are depicted as comprising only a single semiconductor device, multiple semiconductor devices could be coupled in series to perform the same switching function. The method described above to test each leg is equally applicable to legs having multiple switches. Also, the switch elements for switches SW1 to SW4 could be SCRs, IGBTs, MOSFETs, BJTs, MCTs, or any other high voltage semiconductors. Consequently, within the scope of the appended claims, it will be appreciated that the invention can be practiced otherwise than as specifically described herein.

Figure 9:
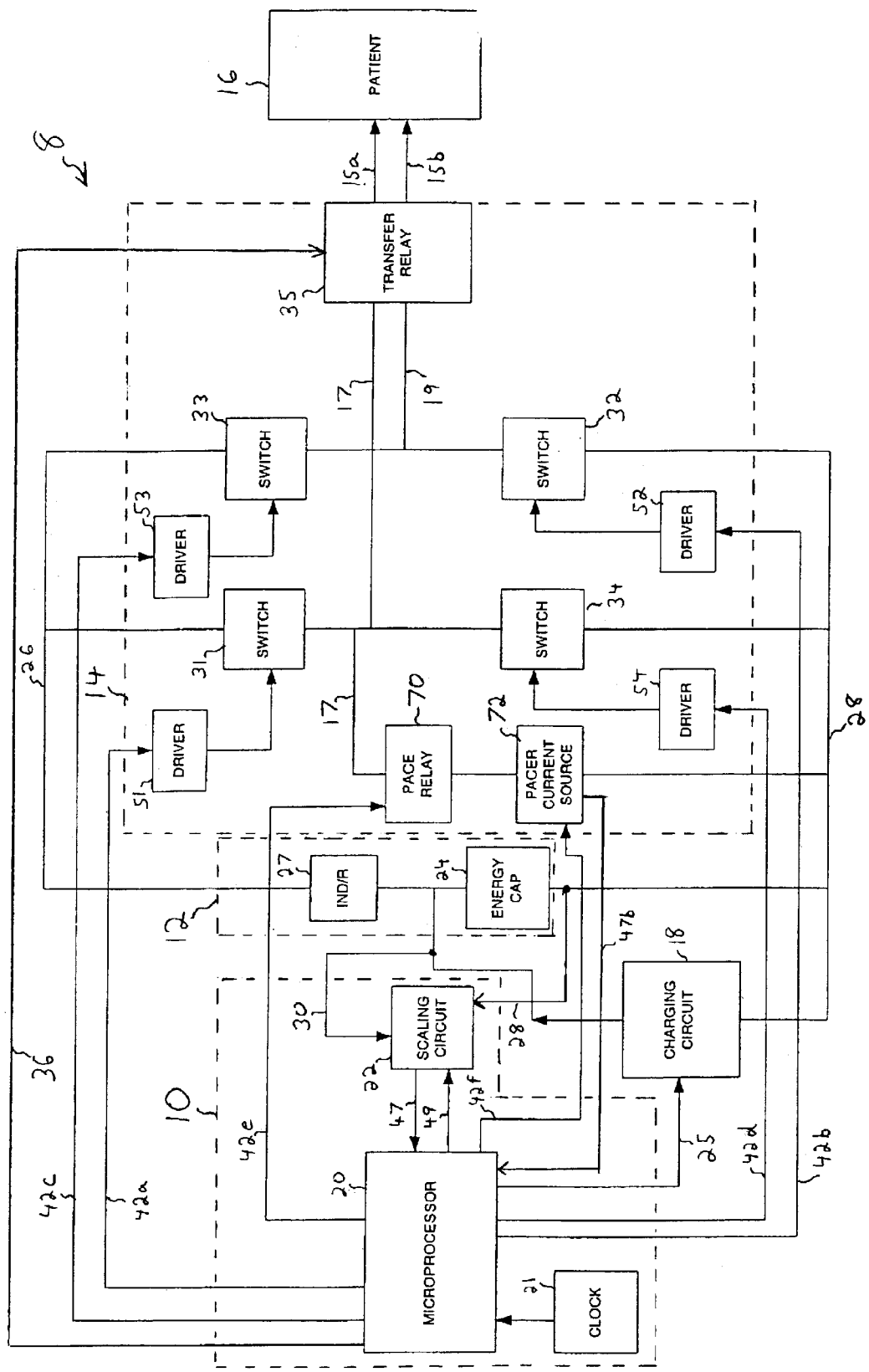
FIG. 9 is a block diagram illustrative of a combined defibrillator/pacer unit having a single output circuit, in accordance with the present invention.

FIG. 9 is a block diagram illustrative of an external combined defibrillator/pacer 8, according to one embodiment of the present invention. Similar components have been given similar reference numbers to those found in FIGS. 1 and 2. The defibrillator/pacer 8 is connected to a patient 16 and includes a microprocessor 20 that is connected to an energy storage capacitor 24 via a charging circuit 18. It will be appreciated by those skilled in the art that energy storage capacitor 24 may be implemented with a multi-capacitor network (i.e., with capacitors connected in series and/or parallel). During the operation of the defibrillator/pacer 8, microprocessor 20 controls charging circuit 18 using a signal on a control line 25 to charge energy storage capacitor 24 to a desired voltage level. To monitor the charging process, microprocessor 20 is connected to a scaling circuit 22 by a measurement line 47, and by a control line 49. It will be understood that while single measurement and control lines are shown, multiple lines may be used. Scaling circuit 22 is connected to energy storage capacitor 24 by a bridge line 28, which connects to the negative lead of energy storage capacitor 24, and by a line 30, which connects to the positive lead of the capacitor. A clock 21 is also connected to microprocessor 20.

After charging to a desired level, the energy stored in energy storage capacitor 24 may be delivered to patient 16 in the form of a defibrillation pulse. H-bridge 14 is provided to allow the controlled transfer of energy from energy storage capacitor 24 to patient 16. H-bridge 14 is an output circuit that includes four switches 31, 32, 33, and 34, which are driven by four driver circuits 51, 52, 53, and 54, respectively. Each switch is connected in a leg of the output circuit that is arrayed in the form of an "H". Switches 31 and 33 are coupled through a protective component 27 to the positive lead of the energy storage capacitor 24 by a bridge line 26. Protective component 27 limits the current and voltage changes from energy storage capacitor 24, and has both inductive and resistive properties. Switches 32 and 34 are coupled to energy storage capacitor 24 by a bridge line 28.

Patient 16 is connected to the left side of H-bridge 14 by an apex line 17, and to the right side of H-bridge 14 by a sternum line 19. As depicted in FIG. 9, apex line 17 and sternum line 19 are connected to electrodes 15a and 15b, respectively, by a transfer relay circuit 35. Microprocessor 20 is connected to driver circuits 51, 52, 53 and 54 by control lines 42a, 42b, 42c, and 42d, respectively, and to transfer relay circuit 35 by control line 36.

A pace relay 70 and pacer current source 72 are connected in series between apex line 17 and bridge line 28. Pace relay 70 and pacer current source 72 are connected to receive control signals from microprocessor 20 through control lines 42e and 42f, respectively. As will be described in more detail below, pace relay 70 and pacer current source 72 are implemented to generate pacing pulses, and operate in combination with switch 33.

As will be described in more detail below, application of appropriate control signals by microprocessor 20 over the control lines causes switches 31–34 to be appropriately opened and closed and pace relay 70 to be opened, thereby allowing H-bridge 14 to conduct energy from energy storage capacitor 24 to patient 16 in the form of a defibrillation pulse. In a similar manner, microprocessor 20, through appropriate application of the control signals, causes switches 31–34 to be appropriately opened and closed and pace relay 70 to be closed and pacer current source 72 to be activated, thereby allowing H-bridge 14 to conduct energy from storage capacitor 24 to the patient in the form of a monophasic pacing pulse. More specifically, switch 33, which in one embodiment is implemented as an SCR, is activated in combination with the pace relay 70 and the pacer current source 72, in order to generate the pacing pulse. The operation and components H-bridge output circuit 14 and certain pacing circuits are described in more detail in U.S. Pat. Nos. 6,208,895 and 6,175,765, each of which are commonly assigned and each of which are hereby incorporated by reference in their entireties.

Figure 10:
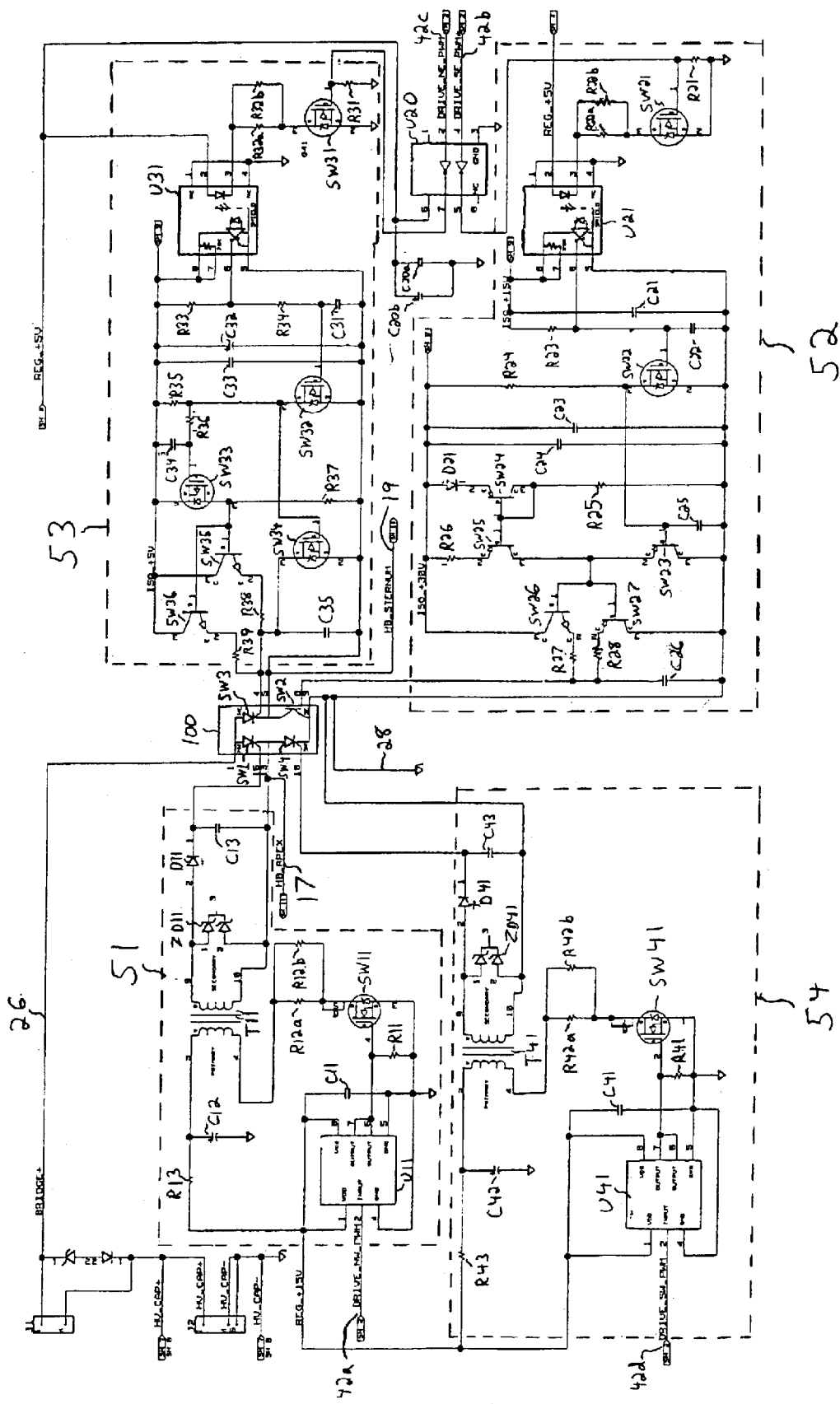
FIG. 10 is a schematic diagram of the H-bridge output circuit of FIG. 9.

A schematic diagram of a preferred construction of H-bridge 14 is shown in FIG. 10. H-bridge 14 uses four output switches SW1–SW4 to conduct energy from energy storage capacitor 24 to patient 16. Switches SW1–SW4 correspond to switches 31–34 of FIG. 9, respectively. Switches SW1, SW3 and SW4 are semiconductor switches, preferably silicon controlled rectifiers (SCRs). Switch SW2 is an insulated gate bipolar transistor (IGBT). Switches SW1–SW4 can be switched from an off (nonconducting) to an on (conducting) condition.

Each of the switches SW1–SW4 is implemented as a single power switch device. Switches SW1–SW4 are packaged in a single surface-mountable package 100 for ease in manufacturing. This circuit package achieves a substantial reduction in overall parts count over previous external defibrillator H-bridges which required multiple switches in each leg, e.g., two or more IGBTs in a leg, and which were not designed to be provided in a single package. The reduction in overall parts count and ease of manufacturing of the single-surface mountable package improves the reliability and manufacturability of the external defibrillator/pacer device 8. In addition, the use of the single IGBT device for a power switch in one of the legs of the H-bridge circuit simplifies the drive circuit requirements for the IGBT over previous H-bridge designs which utilized multiple IGBT devices.

In the defibrillation mode, defibrillator/pacer 8 generates a biphasic defibrillation pulse for application to the patient 16. Initially, switches SW1–SW4 and the pace and transfer relays are opened. Charging of energy storage capacitor 24 is started, and monitored by microprocessor 20 (FIG. 9). When energy storage capacitor 24 is charged to a selected energy level and the transfer relay 35 is closed, switches SW1 and SW2 are switched on so as to connect energy storage capacitor 24 with apex line 17 and sternum line 19 for the application of a first phase of a defibrillation pulse to patient 16. The first phase of the biphasic pulse is therefore a positive pulse from the apex to the sternum of patient 16.

Before energy storage capacitor 24 is completely discharged, switch SW2 is biased off to prepare for the application of the second phase of the biphasic pulse. Once switch SW2 is biased off, switch SW1 will also become nonconducting current though he SCR drops below the holding current for the SCR.

After the end of the first phase of the biphasic defibrillation pulse, switches SW3 and SW4 are switched on to start the second phase of the biphasic pulse. Switches SW3 and SW4 provide a current path to apply a negative defibrillation pulse to patient 16. The polarity of the second phase of the defibrillation pulse is therefore opposite in polarity to the first phase of the biphasic pulse. The end of the second phase of the biphasic pulse is truncated by switching on switch SW1 and switch SW2 to provide a shorted path for the remainder of the capacitor energy through switches SW1 and SW4 and also through switches SW2 and SW3. After energy storage capacitor 24 is discharged, switches SW1–SW4 go to a nonconducting state. Patient isolation relay 35 is then opened. Energy storage capacitor 24 may then be recharged to prepare defibrillator/pacer 8 to apply another defibrillation pulse or to apply pacing pulses.

In the pacing mode, defibrillator/pacer 8 generates a monophasic pacing pulse for application to the patient 16. Initially, switches SW1–SW4 and the pace and transfer relays are opened. Charging of the energy storage capacitor 24 is started, and monitored by the microprocessor 20 (FIG. 9). When the energy storage capacitor 24 is charged to a selected energy level and the transfer relay 35 is closed, the pace relay 70 is closed and the pacer current source 72 and the switch SW3 are switched on so as to connect energy storage capacitor 24 with apex line 17 and sternum line 19 for the application of a pacing pulse to the patient 16. The energy travels from the positive terminal of the energy storage capacitor 24 on line 26, through switch SW3 and sternum line 19, across patient 16, and back through apex line 17 and pace relay 70 and pacer current source 72 to the negative terminal of energy storage capacitor 24 on line 28. The polarity of the pacing pulse is therefore a negative pulse from the apex to the sternum of the patient 16.

As described above, the four output switches SW1–SW4 can be switched from an off (nonconducting) state to an on (conducting) state by application of appropriate control signals on control lines 42a, 42b, 42c, and 42d. In order to allow the SCRs and IGBT to switch the high voltages in an external defibrillator and the low currents for pacer applications, special switch driving circuits 51, 52, 53 and 54 are coupled to switches SW1–SW4, respectively. Control lines 42a, 42b, 42c, and 42d are connected to switch driving circuits 51, 52, 53, and 54, to allow microprocessor 20 to control the state of the switches.

Switch driving circuits 51 and 54 are identical. For purposes of this description, therefore, only the construction and operation of switch driving circuit 51 will be described. Those skilled in the art will recognize that switch driving circuits 51 and 54 operate in a similar manner. Switch driving circuits 51 and 54 are designed to drive the SCR switches SW1 and SW4 so that they are able to both conduct the high-energy defibrillation pulses of 200 or more joules, as well as remaining conducting during low energy defibrillation pulses of at least as low as 1 to 50 joules.

Switch driving circuit 51 includes a control chip U11, a control switch SW11, resistors R11, R12, and R13, capacitors C11, C12, and C13, a diode D11, a component ZD11, and a high-voltage transformer T11. The left side of control chip U11 has pins 1, 2 and 4, while the right side has pins 5, 6, 7 and 8. The left side pins 1, 2 and 4 are for VDD, input, and GND, respectively, while the right side pins 5, 6, 7 and 8 are for VDD, two output pins, and GND, respectively. The input pin 2 is connected to control line 42a. A positive voltage supply REG $V_{15}$+ is coupled to both of the VDD pins 1 and 8. In one embodiment, the positive voltage supply REG $V_{15}$+ is at 15 volts. Ground is connected to both of the GND pins 4 and 5. Both of the output pins 6 and 7 are connected together.

The capacitor C11 is connected between the positive voltage supply REG $V_{15}$+ and ground. The resistor R11 is coupled between the output pin 6 and ground. The gate of the switch SW11 is coupled to the output pin 6, while the source is coupled to ground. The resistors R12a and R12b are coupled in parallel between the drain of the control switch SW11 and the non-dotted end of the primary winding of transformer T11. The capacitor C12 is coupled between the dotted end of the primary winding of the transformer T11 and ground. The resistor R13 is coupled between the dotted end of the primary winding of the transformer T11 and the positive voltage supply REG $V_{15}$+. Resistors R12a, R12b, R13, and capacitor C12 limit and shape the current and voltage waveforms across the primary winding of the transformer T11.

On the secondary winding side of transformer T11, the anode of diode D11 is connected to the dotted end of the secondary winding of transformer T11, and the cathode of diode D11 is coupled to the gate of SCR switch SW1. Capacitor C13 is coupled between the cathode of diode D11 and apex line 17. Apex line 17 is coupled to the non-dotted end of the secondary winding of transformer T11. Component ZD11 is coupled between the dotted and non-dotted ends of the secondary winding of transformer T11. As noted above, the anode of SCR switch SW1 is coupled to the bridge line 26, while the cathode is coupled to apex line 17.

To turn on switch SW1, an oscillating control signal is provided on control line 42a. In this embodiment, the oscillating control signal is a pulse train. The pulse train control signal repeatedly turns control switch SW11 on and off, producing a changing voltage across the primary winding of transformer T11. The voltage is stepped down by transformer T11 and rectified by diode D11 before being applied to the gate of SCR switch SW1. In one embodiment, a 10% duty cycle pulse train on the control line 42a has been found to be adequate to maintain SCR switch SW1 in a conducting state. As long as the control signal is applied to the switch driving circuit 51, the switch SW1 will generally remain in the conducting state. The switch SW1 remains in the conducting state even when conducting relatively low defibrillation currents. In one embodiment, the drive circuits 51 and 54 allow the SCR switches SW1 and SW4 to conduct currents as low as 90 mA. As is well known, once triggered or latched on, an SCR generally remains in the conducting state until the current through the SCR drops below a minimum level (e.g., 90 mA), even if the gate voltage of the SCR is grounded.

IGBT switch SW2 is driven by switch driving circuit 52. Switch driving circuit 52 amplifies the control signal 42b and provides it to the gate of the IGBT switch SW2. It is desirable to drive the IGBT switch SW2 with a high voltage at its gate so that the switch will be able to conduct high currents, as will be described in more detail below. As will also be described in more detail below, it is also desirable to control the turn on and turn off time of the IGBT switch SW2, so as to ensure proper operation of the other switches of the H-bridge 14.

Switch driving circuit 52 includes resistors R21–R28, capacitors C21–C26, switches S21–S27, and an optocoupler U21. Control signal 42b is coupled through an inverter in a component U20 to the switch driving circuit 52. The right side of component U20 has pins 1, 2, 3 and 4, while the right side has pins 5, 6, 7 and 8. The pins 1 and 8 are for NC, while the pin 3 is for GND, and the pin 6 is for VCC. Within the component U20, the pin 2 is coupled through an inverter to the pin 7, while the pin 4 is coupled through another inverter to the pin 5. The GND pin 3 is coupled to ground while the VCC pin 6 is coupled to a positive power supply REG $V_5$+, which in one embodiment may be at +5 volts. Capacitors C20a and C20b are coupled in parallel between pin 6 and ground. As noted above, control signal 42b is coupled to pin 4, which is coupled through an inverter in component U20 to pin 5. Pin 5 is coupled to the input of switch driving circuit 52 at the gate of a control switch SW21.

In switch driving circuit 52, the gate of control switch SW21 is coupled through a resistor R21 to ground, and the source is also coupled to ground. Resistors R22a and R22b are coupled in parallel between the drain of switch S21 and the cathode of an LED which is at a pin 3 of optocoupler U21. On the right side of optocoupler U21 are pins 1–4, which are isolated from pins 5–8 on the left side. The anode of the LED at pin 2 in optocoupler U21 is coupled to the positive voltage supply REG $V_5$+. The two NC pins 1 and 4 are each coupled to ground. Pins 7 and 8 are coupled to the positive voltage power supply ISO $V_{15}$+. Within optocoupler U21, pins 7 and 8 are coupled to one another by a resistor. Pin 6 of optocoupler U21 is coupled by a resistor R23 to the positive voltage supply ISO $V_{15}$+, and to the bridge line 28. Bridge line 28 is referenced as a type of ground potential for the high voltage circuitry of the defibrillator/pacer 8, and is coupled to the negative terminal of the energy storage capacitor 24. Pin 5 is coupled to bridge line 28. A capacitor C21 is coupled between the positive voltage supply ISO $V_{15}$+ and bridge line 28.

Pin 6 of optocoupler U21 is also coupled to the gate of a switch SW22, while the source of switch SW22 is coupled to the bridge line 28. A resistor R24 is coupled between a positive voltage supply ISO $V_{30}$+, and the drain of switch SW22. In one embodiment, the positive voltage supply ISO $V_{30}$+ may be at 30 volts. Capacitors C23 and C24 are coupled in parallel between the positive voltage supply ISO $V_{30}+$ and the bridge line 28. The anode of diode D21 is coupled to the positive voltage supply ISO $V_{30}+$, while the cathode is coupled to the emitter of a switch SW24. The base of switch SW24 is coupled to the base of switch SW25, and is also coupled to the collector of the switch SW24. The collector of switch SW24 is also coupled through a resistor R25 to the bridge line 28. The emitter of switch SW25 is coupled through a resistor R26 to the positive voltage supply ISO $V_{30}+$. The collector of switch SW25 is coupled to the emitter of switch SW23, and also to the bases of switches SW26 and SW27.

The base of switch SW23 is coupled to the drain of switch SW22, and the collector of switch SW23 is coupled to the bridge line 28. The collector of switch SW26 is coupled to the positive voltage supply ISO $V_{30}+$, while the emitter is coupled through a resistor R27 to the gate of IGBT switch SW2. The emitter of switch SW27 is coupled through a resistor R28 to the gate of IGBT switch SW2, while the collector switch SW27 is coupled to the bridge line 28. A capacitor C26 is coupled between the gate of IGBT switch SW2 and the bridge line 28.

It will be appreciated that the optocoupler U21 provides isolation of the high voltage circuitry including IGBT switch SW2, from the low voltage control circuitry including control signal 42b. It will also be appreciated that the switch driving circuit 52 amplifies the control signal 42b for use in driving the gate of the IGBT switch SW2. In one embodiment, the gate of the IGBT switch SW2 may be driven with up to 30 volts, as dictated in part by the positive supply voltage ISO $V_{30}+$.

High currents may sometimes occur in H-bridge 14. One way that high currents may be created is when low resistance is placed between the shock paddles. When this happens, a high current flows between apex line 17 and sternum line 19. In this embodiment, to accommodate high currents without damaging IGBT switch SW2, IGBT switch SW2 may be biased by a high gate voltage (e.g., 30 volts) such that the IGBT can safely conduct upwards of 200 amperes of current.

In one embodiment, the drive circuit 52 is designed so that IGBT switch SW2 is turned on relatively slowly when compared to the fast turn on of SCR switches SW1, SW3, and SW4. A slow turn-on for IGBT switch SW2 is desirable because the IGBT switch is on the same side of H-bridge 14 as SCR switch SW3. SCR switch SW3 is controlled by the control signal on control line 42c, but due to the nature of SCR switches, the SCR switch may be accidentally turned on regardless of the signal on control line 42c if a rapid voltage change occurs across SCR switch SW3. If IGBT switch SW2 was therefore turned on too quickly, the resulting rate of change of the voltage across SCR switch SW3 might cause it to turn on accidentally.

In contrast to the slow turn-on of IGBT switch SW2, the turn-off of the IGBT switch may be performed relatively quickly. The IGBT switch can be quickly turned off because at turn-off there is no concern that the sensitive SCR switches will accidentally turn on.

It will be appreciated that driving circuit 52 allows the IGBT to be used in external defibrillator/pacer 8 where extremely high voltages must be switched in the presence of SCRs. The driving circuit and the use of the single IGBT switch minimizes the number of components required to switch a defibrillation pulse of 200 or more joules. In addition to conducting high currents associated with high-energy defibrillation pulses, the IGBT is also able to conduct very low currents that are associated with defibrillation pulses of as low as 1 to 50 joules.

Switch driving circuit 53 drives SCR switch SW3. As will be described in more detail below, switch driving circuit 53 is designed to be able to drive the SCR for a high current defibrillation pulse, and also maintain the SCR in a conducting state during a low current pacing pulse. The driving circuit 53 is also designed with the desired impedance for driving the SCR switch SW3.

The switch driving circuit 53 includes resistors R31–R39, capacitors C31–C35, switches SW1–SW36, and an optocoupler U31. Optocoupler U31 effectively isolates the high voltage circuitry including SCR switch SW3, from the low voltage control circuitry including control signal 42c. The control signal 42c is coupled through a component U20 to the drive circuit 53. Control signal 42c is coupled to pin 2 of component U20. Within component U20, pin 2 is coupled through an inverter to pin 7, which is coupled to the gate of control switch SW31 of drive circuit 53.

The source of switch SW31 is coupled to ground and the gate is coupled through a resistor R31 to ground. Resistors R32a and R32b are coupled in parallel between the drain of switch SW31 and a pin 3 of optocoupler U31. Optocoupler U31 includes pins 1–4 on the right side, and pins 5–8 on the left side. Pins 1 and 4 are NC pins which are coupled to ground. Within optocoupler U31, pin 3 is coupled to the cathode of an LED and pin 2 is coupled to the anode of the LED. Pin 2 is coupled to the positive voltage supply REG $V_5+$.

Pins 7 and 8 of optocoupler U31 are coupled to a positive voltage supply ISO $V_5+$. Within optocoupler U31, pins 7 and 8 are coupled to one another by a resistor. Pin 5 is coupled to the sternum line 19. Pin 6 is coupled through a resistor R33 to the positive voltage supply ISO $V_5+$. Pin 6 is also coupled through resistor R34 to the gate of switch SW32.

The gate of switch SW32 is also coupled through a capacitor C31 to the sternum line 19. Capacitors C32 and C33 are coupled in parallel between the positive voltage supply ISO $V_5+$ and the sternum line 19. The source of switch SW32 is coupled to the sternum line 19, while the drain is coupled through a resistor R35 to the positive voltage supply ISO $V_5+$. The drain of switch SW32 is coupled to the gate of a switch SW34, and is also coupled through a resistor R36 to the gate of a switch SW33. The gate of switch SW33 is coupled through a capacitor C34 to the positive voltage supply ISO $V_5+$. The drain of switch SW33 is coupled through a resistor R37 to the sternum line 19, and is also coupled to the bases of a switches SW35 and SW36. The source of switch SW33 is coupled to the positive voltage supply ISO $V_5+$.

The source of switch SW34 is coupled to the sternum line 19, while the drain is coupled to the gate of SCR switch SW3. A capacitor C35 is coupled between the gate of SCR switch SW3 and the sternum line 19. The collector of switch SW35 is coupled to the positive voltage supply ISO $V_5+$, while the emitter is coupled through a resistor R38 to the gate of SCR switch SW3. The base of switch SW35 is coupled to the base of switch SW36. The collector of switch SW36 is coupled to the positive voltage supply ISO $V_5+$, while the emitter is coupled through a resistor R39 to the gate of SCR switch SW3.

The operation of drive circuit 53 can be described as follows. When control signal 42c is off, pin 6 of optocoupler U31 goes low, which pulls the gate of switch SW32 low and thus turns off switch SW32. With switch SW32 off, then the gate of switch SW34 is pulled high through the resistor R35, and thus switch SW34 is turned on. With switch SW34 turned on, then the gate of SCR switch SW3 is pulled low, and more specifically, the gate of SCR switch SW3 is shorted to the cathode, thus placing the SCR switch SW3 in a generally nonconducting state.

When control signal 42c is on, pin 6 of optocoupler U31 is pulled high, which causes the gate of switch SW32 to go high. Switch SW32 is thereby turned on, thus causing the gate of switch SW34 to be pulled low, thus turning off switch SW34. With switch SW32 being on, the gate of switch SW33 is pulled low, and since switch SW33 is a P-channel MOSFET, switch SW33 is thereby turned on. This activates switches SW35 and SW36, which provide current amplification and which provide the drive current for the gate of the SCR switch SW3, and thus turns on the SCR switch SW3.

The high driving current for SCR switch SW3 is important for the high energy defibrillation pulses. It is also important for the driving circuit 53 to maintain the SCR switch SW3 in a conducting state for the very low currents which occur during pacing applications. The drive circuit 53 is also designed to match the impedance requirements for driving the SCR switch SW3. In this regard, it should also be noted that when both switches SW35 and SW36 are on, the resistors R38 and R39 are essentially in parallel. In one embodiment, the resistors R38 and R39 may be approximately 21 ohms, so as to produce an overall source impedance of approximately 9 ohms, so as to match the impedance requirements for a particular SCR switch SW3. In other words, the impedance of the drive circuit 53 is selected so as to maintain the load line of the design above the specifications for the SCR switch SW3, so as to ensure that the SCR switch SW3 will remain on in a desired range.

In one embodiment, the defibrillator/pacer 8 is set so that the pacing current is adjustable from 0 to 200 mA, in minimum steps of 10 mA. It should be noted that the drive circuit 53 allows the SCR switch SW3 to remain conducing at these levels, and even at levels far below the 10 mA range. More specifically, the drive circuit 53 provides a relatively high continuous current to the gate of the SCR switch SW3, which in one embodiment may be greater than 100 mA. This high continuous gate to cathode drive current allows the SCR to remain conducting even when the current from the anode to cathode flowing through the SCR switch SW3 is far below the normal holding current for holding on the SCR switch SW3. Thus, for the anode to cathode current, there is essentially no longer a lower limit in practical values for how low of a pacing current could be conducted, since the anode to cathode current required for holding on the SCR is no longer a practical imitation. This is in contrast to previous drive circuits which drove the SCR utilizing driving currents such as a pulse train, for which the SCR switch SW3 might turn off in between the pulses if the anode to cathode current was below the holding current for the SCR. In addition, it should be noted that while a lower drive current such as that used in other SCR driving circuits would conserve more energy, it also would not ensure that the SCR remain conducting for the low current pacing pulses.

Protection for the switches SW1–SW4 is provided in part by protective component 27, which has both inductive and resistive properties. In one embodiment, protective component 27 is implemented with coil of resistance wire that provides an inductive resistance. Protective component 27 limits the rate of change of the voltage across, and current flow to, SCR switches SW1, SW3, and SW4. Too high of a rate of change of the voltage across an SCR switch is undesirable because it can cause the SCR switch to inadvertently turn on. For example, since SCR switches SW1 and SW4 are on the same side of H-bridge 14, any time SCR switch SW4 is abruptly turned on, a rapid voltage change may also result across SCR switch SW1. To prevent rapid voltage changes, protective component 27 reduces the rate of change of the voltage across SCR switch SW1 when SCR switch SW4 is turned on. Also, too high of a current flow can damage the switches SW1, SW3 and SW4, and protective component 27 limits the current flow in H-bridge 14. The use of protective component 27 therefore reduces the need for additional protective components that would otherwise need to be coupled to switches SW1, SW3 and SW4.

It will be appreciated that one advantage of H-bridge 14 described above is that it allows external defibrillator/pacer 8 to generate and apply a high-energy biphasic waveform to a patient. For prior defibrillators providing a monophasic waveform, the standard energy level in the industry for the discharge has been equal to or greater than 200 joules. The above described circuit allows the same amount of energy (approximately equal to or greater than 200 joules) to be delivered to the patient in a biphasic waveform, thereby resulting in a greater certainty of defibrillation effectiveness for a broader range of patients. At the same time, the circuit incorporates special driving circuitry to allow even very low energy biphasic waveforms (e.g., as low as 1 to 50 joules) to be delivered to the patient.

Figure 11:
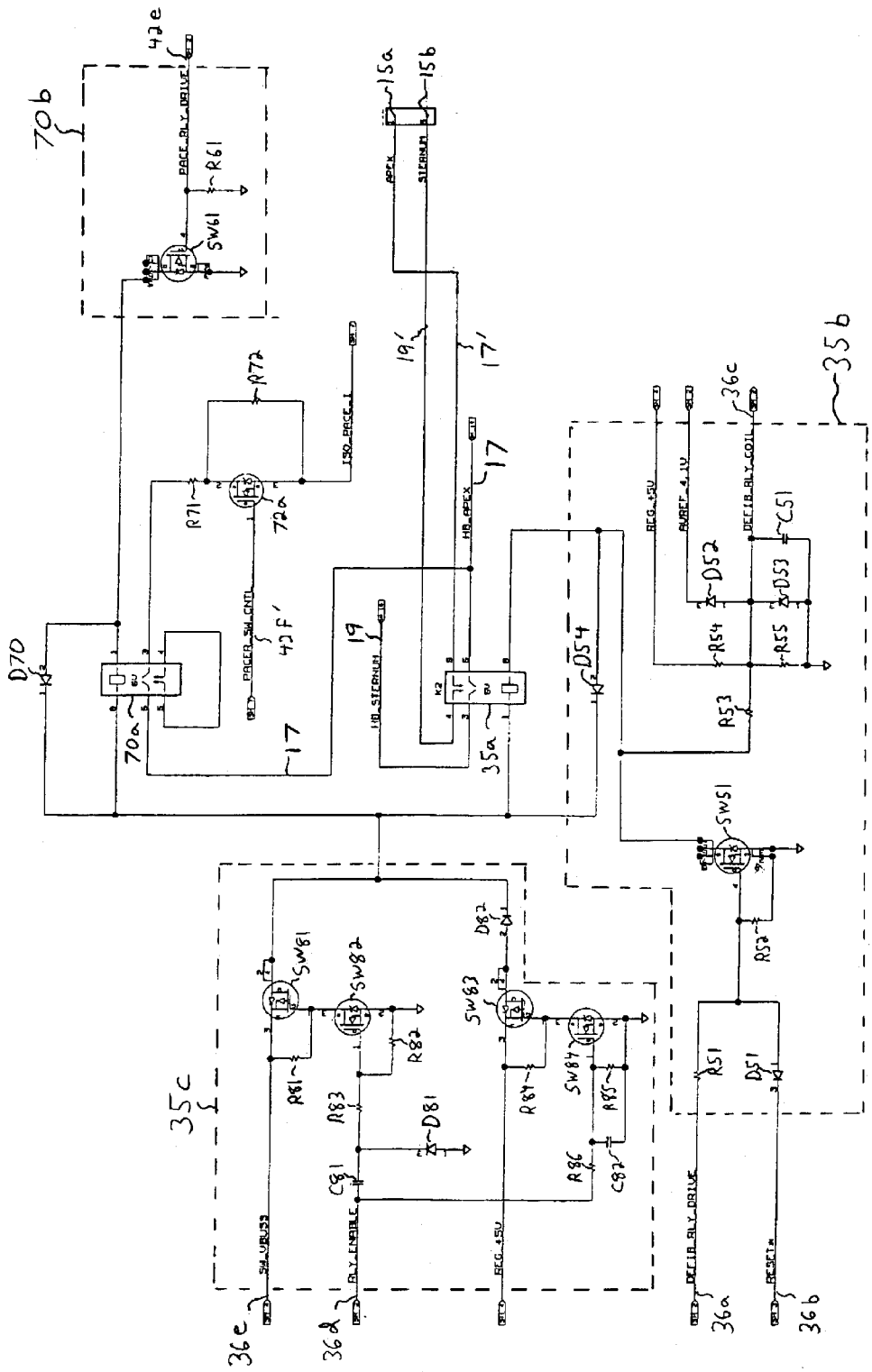
FIG. 11 is a schematic diagram of the transfer and pace relays and the pacer current source of FIG. 9.
Figure 12:
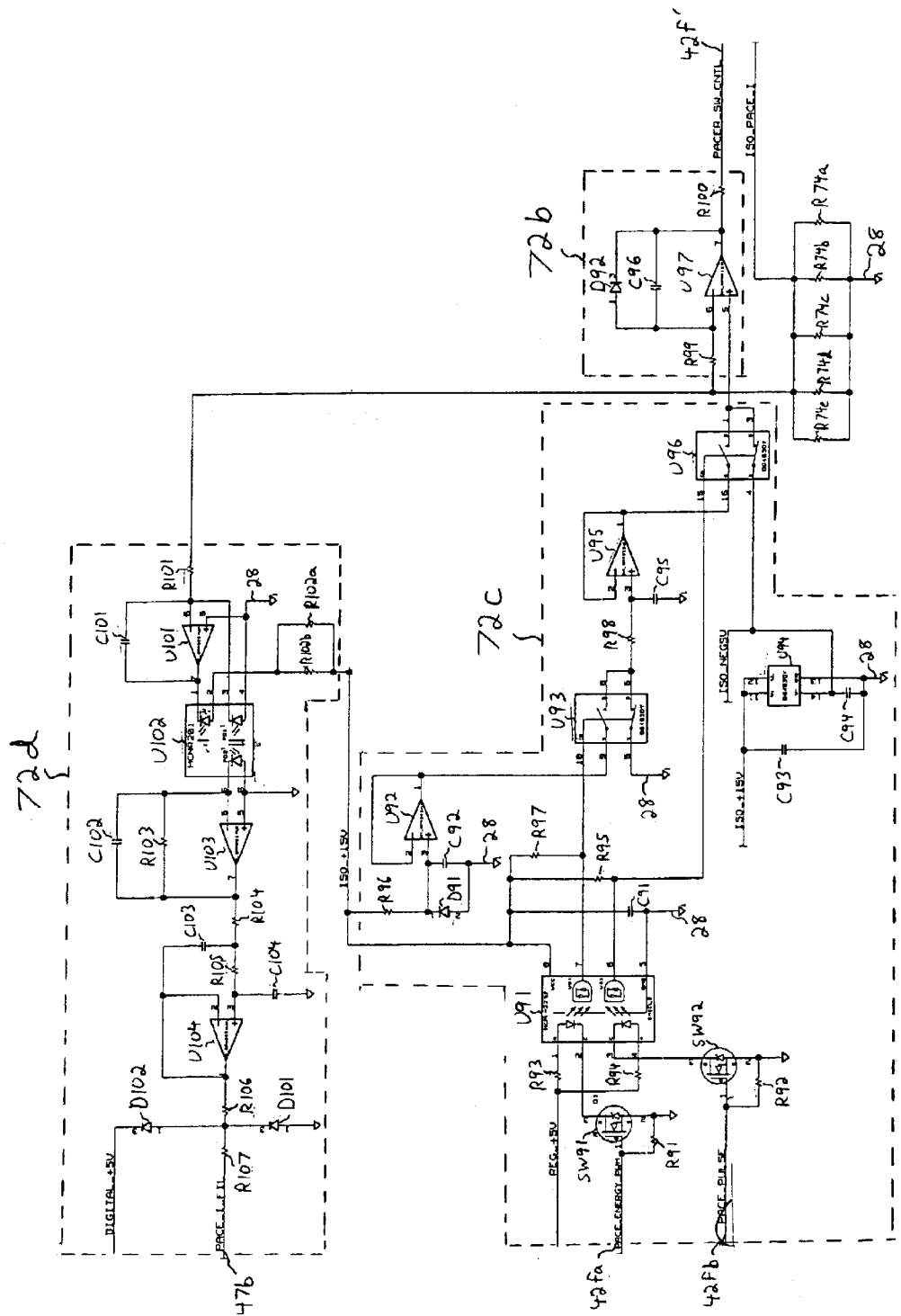
FIG. 12 is a schematic diagram of the control circuitry for the pacer circuitry of FIG. 9.

FIGS. 11 and 12 are schematic diagrams of the transfer relay 35, the pace relay 70, and the pacer current source 72. As shown in FIG. 11, the transfer relay 35 includes a relay 35a which is driven by drive circuits 35b and 35c, which receive the control signals 36a–36e. The pacer relay 70 includes a relay 70a which is driven in part by drive circuits 70b, which receives the control signal 42e. Relay 70a is also driven in part by the same drive circuit 35c which drives relay 35a. The pacer current source 72 includes switch 72a which is driven by drive circuits 72b and 72c, which will be described in more detail below with reference to FIG. 12.

As shown in FIG. 11, relay 35a has pins 1, 3 and 4 on its left side and pins 5, 6, and 8 on its right side. Pin 3 is coupled to sternum line 19, which when the relay is closed is connected to pin 4, which is coupled to a sternum line 19' which may be coupled to electrode 15b. Pin 6 is coupled to apex line 17, which when the relay is closed is connected to pin 5, which is coupled to an apex line 17' which may be coupled to electrode 15a. Pin 1 is coupled to the output of driving circuit 35c, while pin 8 is coupled to the output of driving circuit 35b. The anode of a diode D54 is coupled to pin 8, while the cathode is coupled to pin 1.

Drive circuit 35b includes resistors R51–R54, diodes D51–D54, a capacitor C51, and a control switch SW51. A resistor R51 is coupled between the defibrillator relay drive signal 36a and the gate of control switch SW51. A diode D51 is coupled between a reset signal 36b and the gate of control switch SW51, with the cathode being coupled to the reset signal 36a. Resistor R52 is coupled between the gate and source of control switch SW51. The source of control switch SW51 is coupled to ground, while the drain is coupled to pin 8 of the relay 35a. Resistor R53 is coupled between the drain of control switch SW51 and the anode of diode D52.

Resistor R55, diode D53, and capacitor C51 are coupled in parallel between ground and the anode of diode D52. The anode of diode D52 is coupled to a defibrillator relay coil signal 36c, while the cathode of diode D52 is coupled to a reference voltage AVREF $V_{4.1}$. In one embodiment, the reference voltage AVREF $V_{4.1}$ may be at 4.1 volts. Resistor R54 is coupled between the anode of diode D52 and a positive voltage supply REG $V_5+$. The anode of diode D54 is coupled to pin 8 of the relay 35*a*, while the cathode is coupled to pin 1.

Relay drive circuit 35*c* includes resistors R81–R86, diodes D81 and D82, capacitors C81 and C82, and switches SW81–SW84. The source of switch SW81 is coupled to a SW VBUSS signal 36*e*. The gate of switch SW81 is coupled through a resistor R81 to the source of switch SW81. The drain of switch SW81 is coupled to pin 1 of transfer relay 35*a*, and to pin 8 of pace relay 70*a*. The gate of switch SW81 is coupled to the drain of switch SW82.

The source of switch SW82 is coupled by resistor R82 to the gate of switch SW82. The gate of switch SW82 is coupled through a resistor R83 to the cathode of diode D81. The anode of diode D81 is coupled to ground. A capacitor C81 is coupled between the cathode of diode D81 and a relay enable signal 36*d*.

The relay enable signal 36*d* is also coupled to a resistor R86 through the gate of switch SW84. Capacitor C82 and resistor R85 are coupled in parallel between the gate of switch SW84 and the source of switch SW84. The source of switch SW84 is coupled to ground. The drain of switch SW84 is coupled to the gate of switch SW83. A resistor R84 is coupled between the source of switch SW83 and the gate of switch SW83. A positive voltage supply REG $V_5$+ is coupled to the source of switch SW83. The anode of diode D82 is coupled to the drain of switch SW83, while the cathode is coupled to pin 1 of transfer relay 35*a* and pin 8 of pace relay 70*a*.

Transfer relay 35 is operated such that when the defibrillator 8 is to apply a defibrillation pulse or a pacing pulse to the patient 16, the relay is closed. When the relay is open, it isolates the patient 16 from the rest of the defibrillator/pacer 8 circuitry. As described above, the transfer relay includes drive circuits 35*b* and 35*c* which drive the relay 35*a*. The drive circuit 35*c* is coupled to the high side switch that is common for each coil in each of the relays 35*a* and 70*a*. The drive circuit 35*c* provides increased driving for the relays in order to allow them to be turned on quickly.

Pace relay 70 includes relay 70*a* which is driven by drive circuits 70*b* and 35*c*. Relay 70*a* has pins 1, 3, and 4 on its right side, and pins 5, 6, and 8 on its left side. A diode D70 is coupled between coil pins 1 and 8, with the anode coupled to pin 1. As described above, pin 8 is coupled to the output of drive circuit 35*c*. Pins 5 and 4 are shorted together, while pin 6 is coupled to apex line 17. When the relay 70*a* is closed, pin 6 is coupled to pin 5, and pin 4 is coupled to pin 3. Pin 1 is coupled to the output of drive circuit 70*b* which includes a switch SW61 and a resistor R61. The gate of switch SW61 is coupled to the pace relay drive signal 42*e*. Resistor R61 is coupled between the gate of switch SW61 and ground. The source of switch SW61 is coupled to ground. The drain of switch SW61 is coupled to pin 1 of relay 70*a*.

Pin 3 of relay 70*a* is coupled through a resistor R71 to the drain of pacer current source switch 72*a*. The drain of switch 72*a* is coupled to the source by a resistor R72. The source of switch 72*a* is coupled through a sense resistor R74 to bridge line 28, as will be described in more detail below with reference to FIG. 12. The gate of switch 72*a* is coupled to a pacer SW CNTL signal 42*f*. The control signal 42*f* comes from driver circuits 72*b* and 72*c*, which will be described in more detail below with reference to FIG. 12.

As shown in FIG. 12, driver circuit 72*b* includes resistors R99 and R100, capacitor C96, diode D92, and an operational amplifier U97. Operational amplifier U97 is coupled in a feedback loop configuration with switch 72*a* as part of an adjustable pacer current source. Diode D92 and capacitor C96 are coupled in parallel between the negative input of operational amplifier U97 and the output of operational amplifier U97. Resistor R100 is coupled between the output of operational amplifier U97 and control signal 42*f*. Resistor R99 is coupled between the negative input of operational amplifier U97 and the source of switch 72*a* (FIG. 11). Resistor 74 comprises resistors R74*a*–R74*e* which are coupled in parallel between bridge line 28 and the source of the pacer current source switch 72*a*.

Driver circuit 72*b* receives control signals from driver circuit 72*c*. As will be described in more detail below, driver circuit 72*c* receives control signals 42*f* from the microprocessor 20, converts the signals to transfer them across the isolation barrier, and then reconverts the signals to control the feedback loop of driver circuit 72*b*.

Driver circuit 72*c* includes resistors R91–R98, switches SW91–SW92, capacitors C91–C95, and components U91–U96. Optocoupler U91 includes pins 1–4 on the left side and pins 5–8 on the right side. Within optocoupler U91, pin 1 is coupled to pin 2 by an LED which is sensed at pin 7, and pin 4 is coupled to pin 3 by an LED. which is sensed at pin 6. GND pin 5 is coupled to bridge line 28, while VCC pin 8 is coupled to a positive voltage supply ISO $V_{15}$+.

Pin 1 of optocoupler U91 is coupled through a resistor R93 to a positive voltage supply REG $V_5$+. Pin 4 is coupled through a resistor R94 to the positive voltage supply REG $V_5$+. Pin 2 is coupled to the drain of switch SW91, while pin 3 is coupled to the drain of switch SW92. The gate of switch SW91 is coupled by a resistor R91 to the source of switch SW91, while the gate of switch SW92 is coupled by a resistor R92 to the source of switch SW92. Both of the sources of switches SW91 and SW92 are coupled to ground. The gate of switch SW91 receives a pace energy PWM signal 42*fa*, while the gate switch SW92 receives a pace pulse signal 42*fb*. A capacitor C91 is coupled between pins 5 and 8 of optocoupler U91. Resistor R5 is coupled between pins 6 and 8, while resistor R7 is coupled between pins 7 and 8.

An operational amplifier U92 is coupled to serve as a buffer and essentially provides a 5-volt reference. The negative input of operational amplifier U92 is coupled to its output. A diode D92 and capacitor C92 are coupled in parallel between the positive input of the operational amplifier U92 and the bridge line 28. Resistor R96 is coupled between the positive input at the operational amplifier U92 and the positive voltage source ISO $V_{15}$+.

The switching component U93 includes pins 5, 9 and 10 on its left side and pins 6 and 8 on its right side. Within switching component U93, pin 10 is coupled to a control signal, while pin 9 is coupled to pin 8 by a first switch and pin 5 is coupled to pin 6 by a second switch. Pin 5 is coupled to bridge line 28. Pin 9 is coupled to the output of operational amplifier U92. Pin 10 is coupled to output pin 7 of optocoupler U91. Pin 8 of switching component U93 is shorted to pin 6. A resistor R98 is coupled between pin 6 and the positive input of an operational amplifier U95.

A capacitor C95 is coupled between the positive input of operational amplifier U95 and bridge line 28. The negative input of operational amplifier U95 is coupled to the output of operational amplifier U95. The output of operational amplifier U95 is coupled to a pin 16 of a switching component U96.

Switching component U96 includes pins 15, 16 and 4 on its left side, and pins 1 and 3 on its right side. Within switching component U96, pin 15 is coupled to a control signal, while pin 16 is coupled to pin 1 by a first switch, and pin 4 is coupled to pin 3 by a second switch. Pin 5 is coupled to output pin 6 of optocoupler U91. Pin 4 is coupled to a negative voltage supply ISO $V_5-$. Pins 1 and 3 of switching component U96 are shorted together, and are also coupled to the positive input of operational amplifier U97.

Capacitor C93 is coupled between the positive voltage supply ISO $V_{15}+$ and the bridge line 28. Capacitor C94 is coupled between the negative voltage supply ISO $V_5-$ and the bridge line 28. Component U94 has four pins 11–14, with pins 11 and 12 being coupled to positive voltage supply ISO $V_{15}+$, pin 13 being coupled to bridge line 28, and pin 14 being coupled to the negative voltage supply ISO $V_5-$.

As will be described in more detail below, driver circuit 72b utilizes operational amplifier U97 in a conventional feedback loop as part of the pacer current source 72. Driver circuit 72c receives the analog control signal from the microprocessor, transfers it across the isolation barrier, then converts the signal back to a DC control signal. The signals from the microprocessor 20 (FIG. 9) are pulse width modulated (PWM) signals. Pin 7 of optocoupler U91 provides a duty cycle modulated output, and switching component U96 toggles between a negative 5 volt signal and the output of operational amplifier U95. Operational amplifier U95 includes a resistor capacitor filter which converts the pulse width modulated signal into a DC signal proportional to the duty cycle. The input of the operational amplifier U95 is received from the switching component U93 which is controlled by the pin 7 of optocoupler U91, as described above. The end result is that the control signals 42fa and 42fb from the microprocessor are converted into a DC signal proportional to the duty cycle, which determines the pacer current of the pacer current source 72a of FIG. 11. In other words, the microprocessor is able to control the pacer current in accordance with control signals 42fa and 42fb.

Pacer current source 72 also includes a monitor circuit 72d and a sense resistor 74 which provide the microprocessor 20 with feedback as to the operation of the pacer current source 72. Monitor circuit 72d monitors the voltage on sense resistor R74, which indicates the level of pacer current. As will de described in more detail below, monitor circuit 72d is utilized by the microprocessor 20 to monitor the pacer current to ensure that the control signal 42f is controlling the pacer current properly, and that when a pacing control signal is sent that a pacing pulse is generated.

Monitor circuit 72d includes resistors R101–R107, capacitors C101–C104, diodes D101–D102, and components U101–U104. Resistor R101 is coupled between resistor R74 and the negative input of an operational amplifier U101. A capacitor C101 is coupled between the negative input of operational amplifier U101 and the output of operational amplifier U101. The positive input of operational amplifier U101 is coupled to bridge line 28. The output of operational amplifier U101 is coupled to a pin 1 of an optocoupler U102.

Optocoupler U102 includes pins 1–4 on its right side, and pins 5 and 6 on its left side. Within the optocoupler, pin 2 is coupled to pin 1 by an LED, while pin 4 is coupled to pin 3 by a sensor, and pin 5 is coupled to pin 6 by a sensor. Resistors R102a and R102b are coupled in parallel between pin 2 and positive voltage supply ISO $V_{15}+$. Pin 4 is coupled to bridge line 28, and pin 3 is coupled to the negative input of operational amplifier U101. Pin 5 is coupled to ground and pin 6 is coupled to the negative input of an operational amplifier U103.

A capacitor C102 and a resistor R103 are coupled in parallel between the negative input of operational amplifier U103 and the output of operational amplifier U103. A resistor 104 and a resistor 105 are coupled in series between the output of operational amplifier U103 and the positive input of an operational amplifier U104. A capacitor C103 is coupled between the node between resistors R104 and R105, and the negative input of operational amplifier U104. A capacitor C104 is coupled between the positive input of operational amplifier U104 and ground. The negative input of operational amplifier U104 is coupled to the output of operational amplifier U104.

Resistor R106 is coupled between the output of operational amplifier U104 and the cathode of a diode D101. Diode D101 is coupled between ground and the anode of a diode D102. Diode D102 is coupled between the cathode of diode D101 and the positive voltage supply DIGITAL $V_5+$. A resistor R107 is coupled between the cathode of diode D101 and the output sensor signal 47b.

As described above, the monitor circuit 72d provides the output sensor signal 47b to the microprocessor 20. More specifically, when current from the pacer current source switch 72a flows through sense resistor R74, the voltage at sense resistor 74 is provided to the monitor circuit 72d. The monitor circuit 72d then provides the output signal 47b which indicates the sensed voltage, and thus indicates the current that is flowing through the pacer current source 72.

The overall operation of the pacer current source 72, including switch 72a and circuits 72b, 72c, and 72d, can be described as follows. Switch driving circuit 72b uses a feedback scheme to control switch 72a to achieve a desired output current. Microprocessor 20 monitors the current output by switch 72a through resistor R74 and sensor circuit 72d as previously described and adjusts the voltage level of the control signal at control lines 42f to achieve the desired current level. Capacitor C96 causes switch driving circuit 72a to function in a manner similar to an integrator, with its input signal being the voltage at the source of switch 72a. Thus, when the signal at control line 42f dictates a zero voltage, the output voltage of operational amplifier U97 is zero, causing switch 72a to be non-conductive.

When the voltage dictated by control lines 42f through circuit 72a is positive relative to the voltage at the inverting input lead of operational amplifier U97, the "integrator" operates to increase the voltage at its output lead, which in turn causes switch 72a to be more conductive and pull up the voltage at its source. Because this source voltage is fed back to the inverting input lead of operational amplifier U97, the "integrator" only increases its output voltage until the source voltage is substantially equal to the voltage at the non-inverting input lead. That is, the "virtual ground" effect of operational amplifiers causes the "integrator" to quickly drive the source voltage to be equal to the voltage dictated by control lines 42f.

In a symmetrically opposite manner, when the voltage dictated by control lines 42f is negative relative to the voltage at the inverting input lead of operational amplifier U97, the "integrator" operates to decrease the voltage at its output lead, which in turn causes switch 72a to become less conductive and quickly drive the source voltage of switch 72a to be substantially equal to the voltage dictated by control lines 42f. Diode D92 helps to prevent the voltage at the source of switch 72a from being above the voltage at the gate of switch 72a by more than a diode threshold voltage.

Thus, when the microprocessor 20 wishes to increase the output current of pacer current source switch 72a, the microprocessor 20 increases the signal at control lines 42f. As described above, increasing the signal at control lines 42f causes the output current of switch 72a to increase, which is then detected by the microprocessor in monitoring the voltage across resistor R74 through the sensor circuit 72d. When the output current reaches the desired level, microprocessor 20 can then stop increasing the signal at control lines 42f. Conversely, to decrease the output current of switch 72a, microprocessor 20 causes the signal at control lines 42f to decrease, thereby causing the output current of switch 72a to decrease. When the output current reaches the desired level, microprocessor 20 can then stop decreasing the signal at control lines 42f.

The overall operation of the pace relay 70 in combination with the pacer current source 72 can be described as follows. When conductive, pace relay 70 and pacer current source 72 provide a current path from apex line 17 to bridge line 28. As described above, pace relay 70 includes a relay 70a and a driver circuit 70b, while pacer current source 72 includes a switch 72a and driver circuits 72b and 72c. Relay 70a and switch 72a are turned off and on by driving circuits 70b, and 72b and 72c, in response to control signals from microprocessor 20, which are received on control lines 42e and 42f, respectively. In addition, in this embodiment, microprocessor 20 is connected to monitor the voltage across resistor R74 via monitor circuit 72d during the pacing mode. Microprocessor 20 is configured to provide the control signal over control lines 42f to cause switch driving circuit 72b to operate switch 72a so that the current conducted by switch 72a can be adjusted to a desired level. In one embodiment, the technique used is referred to as a constant current pacing technique, in that the current can be maintained at a constant peak level even if patient impedance changes between pulses and is not adjusted with regard to the energy discharged by energy storage capacitor 24.

In the pacing mode, pace relay 70, pacer current source 72, and switch SW3 are turned on. Pacer current source 72 is controlled by microprocessor 20 (FIG. 9) to provide a desired level of pacing current to apex line 19. In one embodiment, the pacing current is typically increased by about 5 mA with each successive pacing pulse until the pulses are of sufficient strength to cause the heart muscle to contract. Microprocessor 20 controls switch SW3 to be turned on for the desired duration of a pacing pulse. As described above, driver circuit 53 is specially designed to maintain SCR switch SW3 in a conducting state even for the relatively small currents of the pacing pulses.

While the preferred embodiment of the invention has been illustrated and described, it will be appreciated that various changes can be made therein without departing from the spirit and scope of the invention.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. In an external defibrillator for applying a multiphasic defibrillation pulse to a patient through first and second electrodes when said first and second electrodes are coupled to a patient, said external defibrillator including an energy storage device having first and second leads coupled to an output circuit, the output circuit comprising:
   (a) a first leg coupled between the first lead of the energy storage device and the first electrode;
   (b) a second leg coupled between the second lead of the energy storage device and the second electrode;
   (c) a third leg coupled between the first lead of the energy storage device and the second electrode;
   (d) a fourth leg coupled between the second lead of the energy storage device and the first electrode; and
   (e) a plurality of semiconductor switches coupled within the legs of the output circuit, wherein only a single semiconductor switch is included in each leg of the output circuit.

2. The output circuit of claim 1, further comprising:
   a charging system configured to charge said energy storage device to an energy level sufficient to deliver approximately 200 or more joules,
   wherein said output circuit is formed of components capable of delivering a combined energy level of approximately 200 or more joules to the first and second electrodes for application to a patient.

3. The output circuit of claim 1, wherein:
   said output circuit is formed of components such that the current flow for the defibrillation pulse is gated on by a single switching element.

4. The output circuit of claim 1, further comprising:
   a charging system for charging said energy storage device to a combined energy level such that a current of at least approximately 200 amps results if the first and second electrodes are shorted together.

5. The output circuit of claim 1, further comprising:
   a control circuit configured to implement a self-test to verify the integrity of the output circuit, the self-test activating one or more of the output switches and then monitoring for an absence of current in order to verify the integrity.

6. The output circuit of claim 1, further comprising:
   a control circuit configured to implement a self-test to verify the integrity of the output circuit, the self-test monitoring energy flow during a first phase of the multiphasic defibrillation pulse as part of a process for verifying the integrity of the output circuit prior to application of a next phase of the multiphasic defibrillation pulse, and providing a warning if the integrity is not verified.

7. The output circuit of claim 1, wherein each of the switches of the first, third, and fourth legs comprise a silicon controlled rectifier (SCR) having a gate, an anode, and a cathode, the gate being connected for receiving gate signals, the anode and cathode being connected in a circuit path that provides current through the SCR.

8. The output circuit of claim 7, further comprising:
   a control circuit that includes a plurality of gate drive circuits, each of the plurality of gate drive circuits coupled to the gate of one of each of the SCRs.

9. The output circuit of claim 8, wherein a gate signal supplied by each gate drive circuit to the gate of each SCR biases the SCR in the conducting state, the SCR remaining biased in the conducting state as long as the gate signal is present.

10. The output circuit of claim 9, wherein at least one of the gate drive circuits produces a pulse train and supplies said pulse train to the gate of the associated SCR as a gate signal.

11. The output circuit of claim 7, wherein the switch in the second leg comprises an insulated gate bipolar transistor (IGBT), the IGBT having a gate, a collector, and an emitter, the gate being connected for receiving gate signals, the collector and emitter being connected in a circuit path to provide current through the IGBT.

12. The output circuit of claim 1, further comprising:
   a control circuit coupled to, and configured to, place the switches in the first leg and the fourth leg in a conducting state to shunt energy from the energy storage device.

13. The output circuit of claim 1, further comprising:
a control circuit coupled to, and configured to, place the switches in the second leg and the third leg in a conducting state to shunt energy from the energy storage device.

14. The output circuit of claim 1, further comprising:
a protective component coupled between the energy storage device and the output circuit, the switches in the first, second, third, and fourth legs having a voltage across them that has a rise time that is determined by the amount of time it takes for the voltage across the switches to develop to a selected level, the protective component having both inductive and resistive properties so as to limit a current to, and a rise time of the voltage across at least one of the switches in the first, second, third, or fourth legs.

15. The output circuit of claim 1, further comprising a control circuit, wherein the control circuit controls the output circuit such that:
during a defibrillation mode, the output circuit supplies a defibrillation pulse to the first and second output leads, and
during a pacing mode, the output circuit supplies a pacing pulse to the first and second output leads.

16. The circuit of claim 15, wherein one of the switches in one of the legs of the output circuit conducts pacing pulses during the pacing mode.

17. The circuit of claim 1, wherein the switches are driven so that they are capable of conducting a least approximately 200 amperes of current.

18. The circuit of claim 1, wherein the switches are driven so that they are capable of conducting defibrillation pulses of as high as 200 or more joules and as low as 50 or less joules.

19. The circuit of claim 1, wherein the switches are driven so that they are capable of conducting external defibrillation pulses of as low as 1 joule.

20. An output circuit of an external defibrillator for applying pulses to a patient, the output circuit comprising:
an H-bridge output circuit comprising first, second, third and fourth legs;
a plurality of semiconductor switches coupled within the legs of the H-bridge output circuit, wherein all of the switches of the H-bridge output circuit are contained within a single surface mountable package; and
a control circuit,
wherein the control circuit controls the output circuit such that:
during a defibrillation mode, the output circuit supplies a defibrillation pulse, and
during a pacing mode, the output circuit supplies a pacing pulse.

21. The output circuit of claim 20, wherein each leg of the H-bridge output circuit comprises only a single semiconductor switch.

22. The output circuit of claim 20, wherein each of the switches of the first, third, and fourth legs comprise a silicon controlled rectifier (SCR) having a gate, an anode, and a cathode, the gate being connected for receiving gate signals, the anode and cathode being connected in a circuit path that provides current through the SCR.

23. The output circuit of claim 20, wherein the switch in the second leg comprises an insulated gate bipolar transistor (IGBT), the IGBT having a gate, a collector, and an emitter, the gate being connected for receiving gate signals, the collector and emitter being connected in a circuit path to provide current through the IGBT.

\* \* \* \* \*